US011278514B2

(12) United States Patent
So et al.

(10) Patent No.: US 11,278,514 B2
(45) Date of Patent: Mar. 22, 2022

(54) COMPOSITION COMPROMISING DUNNIONE AS EFFECTIVE INGREDIENT FOR PREVENTION OR ALLEVIATION OF HAIR LOSS

(71) Applicant: NADIANBIO LTD., Iksan-si (KR)

(72) Inventors: Hong-Seob So, Iksan-si (KR);
Hyung-Jin Kim, Iksan-si (KR);
Dipendra Khadka, Iksan-si (KR);
Gi-Su Oh, Iksan-si (KR); Seung-Hoon Lee, Iksan-si (KR)

(73) Assignee: NADIANBIO LTD., Iksan-si (KR)

( * ) Notice: Subject to any disclaimer, the term of this patent is extended or adjusted under 35 U.S.C. 154(b) by 0 days.

(21) Appl. No.: 16/963,057

(22) PCT Filed: Jan. 18, 2019

(86) PCT No.: PCT/KR2019/000780
§ 371 (c)(1),
(2) Date: Jul. 17, 2020

(87) PCT Pub. No.: WO2019/143192
PCT Pub. Date: Jul. 25, 2019

(65) Prior Publication Data
US 2020/0345683 A1 Nov. 5, 2020

(30) Foreign Application Priority Data
Jan. 18, 2018 (KR) ........................ 10-2018-0006600

(51) Int. Cl.
*A61K 31/343* (2006.01)
*A61P 17/14* (2006.01)

(52) U.S. Cl.
CPC ............ *A61K 31/343* (2013.01); *A61P 17/14* (2018.01)

(58) Field of Classification Search
CPC .............................. A61K 31/343; A61P 17/14
See application file for complete search history.

(56) References Cited

U.S. PATENT DOCUMENTS

| 5,886,027 | A | 3/1999 | Khambay et al. | |
|---|---|---|---|---|
| 9,066,922 | B2 | 6/2015 | Yoo et al. | |
| 2004/0071775 | A1* | 4/2004 | Jiang .................. | A61K 47/6951 424/486 |
| 2005/0010060 | A1 | 1/2005 | Blokhin et al. | |
| 2018/0098960 | A1 | 4/2018 | So et al. | |
| 2019/0083453 | A1 | 3/2019 | So et al. | |

FOREIGN PATENT DOCUMENTS

| KR | 10-2016-0123773 A | 10/2016 |
|---|---|---|
| KR | 10-2017-0055626 A | 5/2017 |
| KR | 10-2017-0124102 A | 11/2017 |
| WO | 97/31936 A2 | 9/1997 |
| WO | 2008/066301 A1 | 6/2008 |
| WO | 2009/048251 A2 | 4/2009 |

OTHER PUBLICATIONS

Hair Loss and Chemotherapy, available Oct. 22, 2012 at https://web.archive.org/web/20121022224637/https://chemocare.com/chemotherapy/side-effects/hair-loss-and-chemotherapy.aspx (Year: 2012).*
Beta-lapachone.com, downloaded from http://www.beta-lapachone.com/brown-adipose-cells/ on Aug. 16, 2022; available on the internet Aug. 3, 2016. (Year: 2016).*
SciFinder_Search_dunnione_8-16-2021.pdf (Year: 2021).*
Google_search_8-16-2021_lapachone_treat_alopecia (Year: 2021).*
Google_search_8-16-2021_MB12662_structure (Year: 2021).*
D. Batchelor, "Hair and cancer chemotherapy: consequences and nursing care—a literature study", European Journal of Cancer Care, 2001, pp. 147-163, vol. 10.
Elizabeth L. McGarvey et al., "Psychological Sequelae and Alopecia Among Women with Cancer", Cancer Practice, Nov./Dec. 2001, pp. 283-289, vol. 9, No. 6.
Aihua Shen et al., "NAD+ augmentation ameliorates acute pancreatitis through regulation of inflammasome signalling", Scientific Reports, Jun. 7, 2017, pp. 1-13, vol. 7, No. 3006.
David Spiegel et al., "Depression and Cancer: Mechanisms and Disease Progression", Biol Psychiatry, 2003, pp. 269-282, vol. 54.
R.M. Trüeb, MD, "Chemotherapy-Induced Hair Loss", STL, Aug. 1, 2010, 9 pgs., vol. 15, No. 7.
Arpana Pandit et al., "Dunnione ameliorates cisplatin-induced small intestinal damage by modulating NAD4 metabolism", Biochemical and Biophysical Research Communications, Oct. 21, 2015, pp. 697-703, vol. 467.
International Search Report for PCT/KR2019/000780, dated Apr. 19, 2019 (PCT/ISA/210).
Haslam et al., "Oxidative Damage Control in a Human (Mini-) Organ: Nrf2 Activation Protects against Oxidative Stress-induced Hair Growth Inhibition", Journal of Investigative Dermatology, vol. 137, 2017 (published online Oct. 1, 2016), pp. 295-304 (10 pages).
Bodo et al. "Cell Injury, Repair, Aging and Apoptosis Dissecting the Impact of Chemotherapy on the Human Hair Follicle A Pragmatic in Vitro Assay for Studying the Pathogenesis and Potential Management of Hair Follicle Dystrophy", The American Journal Of Pathology, vol. 171, No. 4, Oct. 2007, pp. 1153-1167 (16 pages).

(Continued)

*Primary Examiner* — Michael P Cohen
(74) *Attorney, Agent, or Firm* — Sughrue Mion, PLLC

(57) ABSTRACT

A new use of dunnione compound, a pharmaceutically acceptable salt thereof, a prodrug thereof, a solvate thereof, or an isomer thereof as an effective ingredient for prevention or alleviation of hair loss is disclosed. The dunnione compound, a pharmaceutically acceptable salt thereof, a prodrug thereof, a solvate thereof, or an isomer thereof, in an animal model, showed an effective reduction of hair thinning as well as an effective reduction in loss of hair follicles and inner root sheaths. Thus, the duunione compound, a pharmaceutically acceptable salt thereof, a prodrug thereof, a solvate thereof, or an isomer thereof can be used effectively to treat hair loss and/or loss of hair follicles and inner root sheaths, promoting hair regrowth. The hair loss may be caused by anticancer therapy.

6 Claims, 14 Drawing Sheets

(56) References Cited

OTHER PUBLICATIONS

Alfredo Rossi et al., "Chemotherapy-induced alopecia management: clinical experience and practical advice", Journal of Cosmetic Dermatology, Dec. 1, 2017, vol. 16, No. 4, pp. 537-541 (9 pages total).
Hyung-Jin Kim et al., "Dunnione ameliorates cisplatin ototoxicity through modulation of NAD+ metabolism",Hearing Research,Sep. 1, 2015, vol. 333, Sep. 1, 2015, pp. 235-246 (12 pages total).
Jinlei Bian et al., "Synthesis and evaluation of (±)—dunnione and its ortho-quinone analogues as substrates for NAD(P)H:quinone oxidoreductase 1 (NQ01)", Bioorganic & Medicinal Chemistry Letters, Mar. 1, 2015, vol. 25, No. 6, pp. 1244-1248 (5 pages total).
T. Grant Phillips, MD et al., "Hair Loss: Common Causes and Treatment", American Family Physician, Sep. 15, 2017, vol. 96, No. 6, pp. 371-378 (8 pages total).

\* cited by examiner

COMPOSITION COMPROMISING DUNNIONE AS EFFECTIVE INGREDIENT FOR PREVENTION OR ALLEVIATION OF HAIR LOSS

CROSS REFERENCE TO RELATED APPLICATIONS

This application is a National Stage of International Application No. PCT/KR2019/000780 filed Jan. 18, 2019, claiming priority based on Korean Patent Application No. 10-2018-0006600, filed Jan. 18, 2018.

TECHNICAL FIELD

The present invention relates to a pharmaceutical composition for prevention or amelioration of hair loss, comprising, as an active ingredient, a dunnione compound, a pharmaceutically acceptable salt thereof, a prodrug thereof, a solvate thereof, or an isomer thereof.

BACKGROUND ART

Cancer is one of human health and life-threatening diseases, and the incidence thereof has been increasing. Treatment methods for cancer include surgery, radiation therapy, biotherapy, chemotherapy, and the like. Among these, anticancer drugs used in chemotherapy exhibit cytotoxicity on cancer cells in such a way that these drugs intervene in metabolic pathways of the cancer cells and directly interact with DNA, thereby blocking replication, transcription, and translation processes of DNA or interfering with synthesis of nucleic acid precursors, and inhibit cell division.

However, chemotherapy in cancer patients has many adverse effects such as anemia and hypocytosis, caused by bone marrow suppression, gastrointestinal disorders including nausea, vomiting, diarrhea, and the like, and hair loss. Chemotherapy-induced alopecia (CIA), which is experienced by about 65% to 70% of cancer patients, is known to be one of the most psychologically shocking adverse effects for the patients. In addition, CIA leads to changes in appearance and thus causes psychological shock to patients. Also, CIA causes awkwardness, sadness, disgust, anger, depression, or the like in patients, which results in loss of confidence or sexual attraction.

In particular, hair loss keeps patients aware of the disease of cancer and undergoing negative mood swings. In addition, hair loss causes, along with psychological atrophy, difficulties in interpersonal relations, which not only leads to physical and mental pain, but ultimately has a negative impact on the quality of life. Such hair loss is particularly severe in women. Reports have shown that 47% of female cancer patients consider hair loss the most serious adverse effect of chemotherapy, and about 8% of the patients refuse chemotherapy because of the fear of hair loss (McGarvey E L et al., *Cancer Pract.*, 2001; 9: 283-289). In addition, studies have shown that negative psychological effects of CIA may suppress the patient's immune function and cause progression of cancer (Spiegel D et al., *Biol Psychiatry*, 2003; 54: 269-282).

The incidence and extent of CIA vary depending on the anticancer drug's type, half-life, dose, route of administration, rate of administration, and dosage schedule. However, many anticancer drugs used in chemotherapy are known to cause CIA. In particular, anti-cancer drugs that often cause CIA include adriamycin, cyclophosphamide, docetaxel, daunorubicin, epirubicin, etoposide, ifosfamide, irinotecan, paclitaxel, topotecan, vindesine, and vinorelbine. Also, anticancer drugs, which are known to cause CIA in some cases, include amsacrine, bleomycin, busulphan, cytarabine, 5-fluorouracil, gemcitabine, lomustine, melphalan, thiotepa, vinblastine, and the like (Trueb R M., *Skin Therapy Lett.*, 2010; 15(7): 5-7).

Specifically, it has been reported that antimicrotubule agents such as paclitaxel cause CIA in 80% or more of patients, topoisomerase inhibitors such as adriamycin in 60% to 100% of patients, alkylating agents including cyclophosphamide in 60% or more of patients, and antimetabolite agents such as 5-fluorouracil in 10% to 50% of patients, and that CIA occurs more frequently and severely in a case where two or more anticancer drugs are administered in combination than a case where a single drug is administered (Batchelor D., *Eur J Cancer Care*, 2001; 10: 147-163). Although chemotherapy-induced alopecia (CIA) is a major adverse effect that may affect not only individual patients but also society as a whole, there is no effective treatment to date.

On the other hand, dunnione is a naphthoquinone-based compound, and is divided into two structures: alpha-dunnione (2,3-dihydro-2,3,3-trimethyl-naphtho[1,2-b]furan-4,9-dione) and dunnione (2,3-dihydro-2,3,3-trimethyl-naphtho[1,2-b]furan-4,5-dione). In addition, dunnione is obtained from the leaves of *Streptocarpus dunnii*, native to South America, or from some types of Calceolaria. Regarding the pharmacological action of dunnione, the following has been reported to date: dunnione increases activity of the enzyme, NAD(P)H: quinone oxidoreductase 1 (NQO1), and thus leads to an increase in intracellular $NAD^+$ and the like, so that deacetylases, such as Sirtuin 1 that uses such $NAD^+$ as a coenzyme, and the like are activated, which makes dunnione effective in prevention and treatment of small intestinal mucosal damage caused by anticancer drugs, acute pancreatitis caused by alcohol, gallstones in the pancreatic duct, or the like, and the like (Pandit et al., *Biochem Biophys Res Commun*, 2015; 467: 697-703; Shen et al., *Sci Rep*, 2017; 7: 3006). In addition, U.S. Pat. No. 9,066,922 B2 discloses that dunnione can be used for prevention and treatment of obesity, diabetes, metabolic syndrome, neurodegenerative diseases, and mitochondrial dysfunction-related diseases.

DISCLOSURE OF INVENTION

Technical Problem

As a result of making efforts to find a substance effective for amelioration of chemotherapy-induced alopecia, the present inventors have identified that dunnione, known as a substrate for the enzyme NQO1, ameliorates alopecia caused by single or combined administration of anticancer drugs, and thus have completed the present invention.

Solution to Problem

In order to achieve the above object, in an aspect of the present invention, there is provided a pharmaceutical composition for prevention or amelioration of hair loss, comprising, as an active ingredient, a compound represented by Formula 1, a pharmaceutically acceptable salt thereof, a prodrug thereof, a solvate thereof, or an isomer thereof:

[Formula 1]

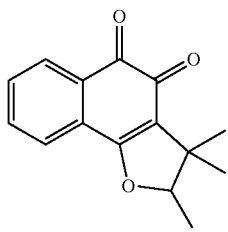

In another aspect of the present invention, there is provided a composition for promoting hair growth, comprising, as an active ingredient, a compound represented by Formula 1, a pharmaceutically acceptable salt thereof, a prodrug thereof, a solvate thereof, or an isomer thereof:

[Formula 1]

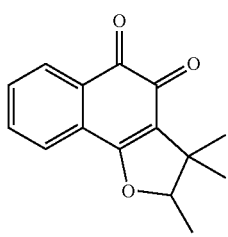

In yet another aspect of the present invention, there is provided a use of the pharmaceutical composition of the present invention for preventing or ameliorating hair loss.

In still yet another aspect of the present invention, there is provided a use of the pharmaceutical composition of the present invention for manufacturing a medicament for prevention or treatment of hair loss.

In still yet another aspect of the present invention, there is provided a method for preventing or ameliorating hair loss, comprising a step of applying the pharmaceutical composition of the present invention.

Advantageous Effects of Invention

In the present invention, an animal model having alopecia caused by administration of cyclophosphamide alone, or an animal model having alopecia caused by combined administration of docetaxel, adriamycin, and cyclophosphamide was administered dunnione, a naphthoquinone-based compound. As a result, it was identified that hair loss is inhibited and falling-off of hair follicles and inner root sheaths is suppressed in such animal models. Accordingly, the dunnione compound, a pharmaceutically acceptable salt thereof, a prodrug thereof, a solvate thereof, or an isomer thereof can be effectively used in a pharmaceutical composition for prevention or amelioration of chemotherapy-induced alopecia.

BEST MODE FOR CARRYING OUT THE INVENTION

Figure 1:
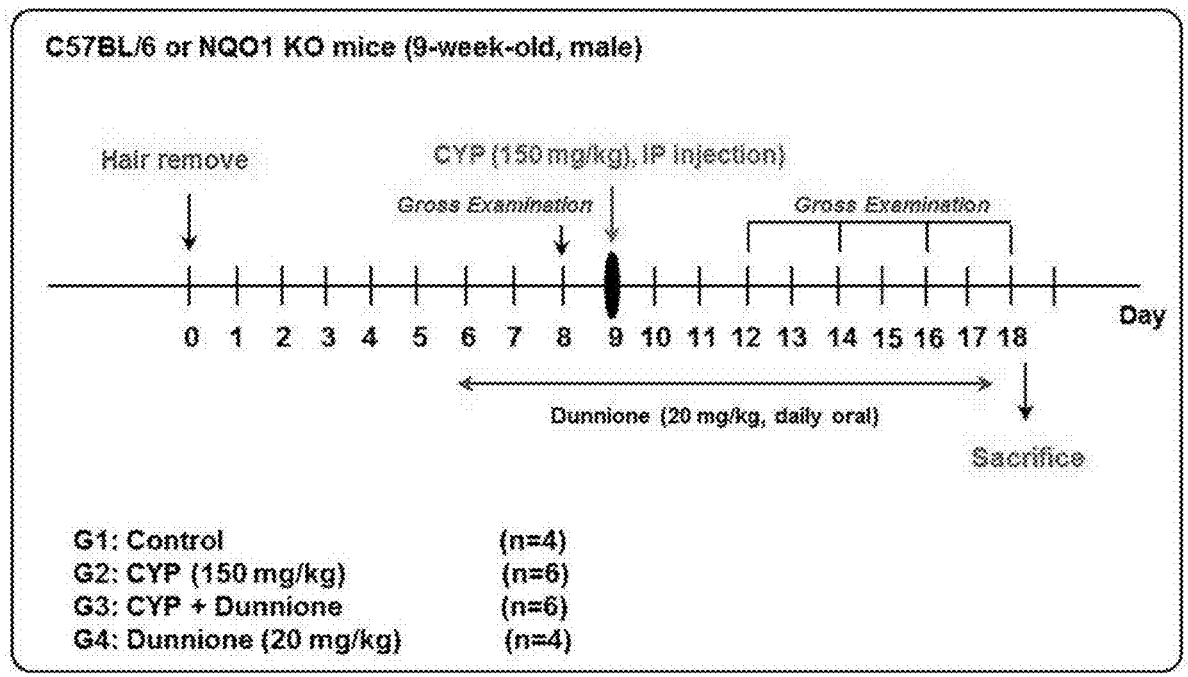
FIG. 1 illustrates an experimental plan for identifying a hair loss inhibitory effect of dunnione in an animal model having alopecia caused by cyclophosphamide.

Hereinafter, the present invention will be described in detail.

In an aspect of the present invention, there is provided a pharmaceutical composition for prevention or amelioration of hair loss, comprising, as an active ingredient, a compound represented by Formula 1, a pharmaceutically acceptable salt thereof, a prodrug thereof, a solvate thereof, or an isomer thereof:

[Formula 1]

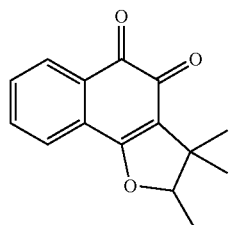

As used herein, the term "pharmaceutically acceptable salt" refers to a formulation of a compound that does not cause significant irritation to an organism to which it is administered and does not abrogate the biological activity and properties of the compound. The pharmaceutical salts include acid addition salts formed with acids that form non-toxic acid addition salts containing a pharmaceutically acceptable anion, for example, inorganic acids such as hydrochloric acid, sulfuric acid, nitric acid, phosphoric acid, hydrobromic acid, hydroiodic acid, and the like, organocarbonic acids such as tartaric acid, formic acid, citric acid, acetic acid, trichloroacetic acid, trifluoroacetic acid, gluconic acid, benzoic acid, lactic acid, fumaric acid, maleic acid, salicylic acid, and the like, and sulfonic acids such as methanesulfonic acid, ethanesulfonic acid, benzenesulfonic acid, p-toluenesulfonic acid, and the like. For example, pharmaceutically acceptable carboxylic acid salts include metal salts or alkaline earth metal salts, formed by lithium, sodium, potassium, calcium, magnesium, or the like, salts of amino acids such as lysine, arginine, and guanidine, and organic salts such as dicyclohexylamine, N-methyl-D-glucamine, tris(hydroxymethyl)methylamine, diethanolamine, choline, and triethylamine. The compound represented by Formula 1 according to the present invention may also be converted to its salt by a conventional method.

As used herein, the term "prodrug" refers to an agent that is converted into the parent drug in vivo. Prodrugs are often used because they are easier to administer than the parent drug. For example, these prodrugs may be bioavailable by oral administration, whereas the parent drug may not. The prodrugs may also have improved solubility in pharmaceutical compositions over the parent drug. For example, the prodrug would be a compound which is administered as an ester (prodrug) to facilitate transport across a cell membrane where water solubility is detrimental to mobility, but which then is metabolically hydrolyzed to carboxylic acid, an active entity, once inside the cell where water solubility is beneficial. A further example of the prodrug might be a short peptide (polyamino acid) bonded to an acidic group where the peptide is metabolized to reveal the active moiety.

As used herein, the term "solvate" refers to a compound of the present invention or a salt thereof which further includes a stoichiometric or non-stoichiometric amount of a solvent bound by non-covalent intermolecular forces. Preferred solvents therefor are solvents that are volatile, non-toxic, and/or acceptable for administration to humans. In a case where the solvent is water, the solvate means hydrate.

As used herein, the term "isomer" refers to a compound of the present invention or a salt thereof which has the same chemical formula or molecular formula but is optically or sterically different therefrom.

Hereinafter, unless otherwise specified, the term "compound represented by Formula 1" is used as a concept including all of the compound itself, a pharmaceutically acceptable salt thereof, a prodrug thereof, a solvate thereof, and an isomer thereof.

The pharmaceutical composition may be administered in a therapeutically effective amount. As used herein, the term "therapeutically effective amount" refers to an amount of an administered compound (active ingredient) which is effective in alleviating or reducing, to some extent, one or more symptoms of the disorder to be treated, or in delaying initiation of symptoms or clinical markers of the disease to be prevented. Thus, the therapeutically effective amount means an amount having the effect of (i) reversing the rate of progress of the disease, (ii) prohibiting, to some extent, further progress of the disease, and/or (iii) alleviating, to some extent, (preferably removing) one or more symptoms associated with the disease. The therapeutically effective amount may be empirically determined by performing experiments with the compound in known in vivo and in vitro model systems for the disease to be treated.

The pharmaceutical composition that comprises, as an active ingredient, the dunnione compound of the present invention, a pharmaceutically acceptable salt thereof, a prodrug thereof, a solvate thereof, or an isomer thereof may be prepared as a formulation for oral administration and administered orally. The formulations for oral administration include, for example, tablets, pills, hard/soft capsules, liquids, suspensions, emulsifiers, syrups, granules, elixirs, and the like, and these formulations further contain, in addition to the active ingredient, diluents (for example, lactose, dextrose, sucrose, mannitol, sorbitol, cellulose, and/or glycine) and lubricants (for example, silica, talc, stearic acid and magnesium or calcium salts thereof, and/or polyethylene glycol). Tablets may also contain binding agents such as magnesium aluminum silicate, starch paste, gelatin, methylcellulose, sodium carboxymethylcellulose, and/or polyvinylpyrrolidone, and may, if necessary, contain disintegrating agents such as starch, agarose, and alginic acid or sodium salts thereof, or boiling mixtures, and/or absorbents, coloring agents, flavors, and sweeteners.

The pharmaceutical composition that comprises, as an active ingredient, the dunnione compound of the present invention, a pharmaceutically acceptable salt thereof, a prodrug thereof, a solvate thereof, or an isomer thereof may be administered parenterally, and the parenteral administration may be achieved by subcutaneous injection, intravenous injection, intramuscular injection, or intrathoracic injection. Here, in a case of being formulated into preparations for parenteral administration, the pharmaceutical composition that comprises, as an active ingredient, the dunnione compound of the present invention, a pharmaceutically acceptable salt thereof, a prodrug thereof, a solvate thereof, or an isomer thereof may be mixed with a stabilizer or a buffering agent in water to produce a solution or suspension, which may in turn be made into unit-dose ampoules or vials. The composition may be sterile and/or may further contain preservatives, stabilizers, hydrating agents or emulsifiers, adjuvants such as salts and/or buffers for adjusting osmotic pressure, and other therapeutically useful substances. The composition may be made into preparations by a conventional method such as mixing, granulation, or coating.

In addition, a human dose of the composition of the present invention may vary depending on the patient's age, body weight, sex, dosage form, health condition, and severity of disease. The dose is generally 0.001 mg/day to 2,000 mg/day, and preferably 0.01 mg/day to 1,000 mg/day, based on an adult patient having a body weight of 60 kg; and the dose may be administered once to several times a day at regular time intervals at the discretion of a doctor or pharmacist. The pharmaceutical composition according to the present invention contains the dunnione compound in an amount of about 0.01% to 100% by weight; however, the amount may vary depending on the dosage form.

The hair loss may be caused by genetic causes, hormones, autoimmune diseases, stress, nutritional deficiencies, drug use, childbirth, fever, surgery, or the like. Specifically, the hair loss may be hair loss caused by drug use, and may preferably be chemotherapy-induced alopecia.

The chemotherapy may be performed by administration of a single anticancer drug or combined administration of two or more anticancer drugs. In a case of the combined administration, the two or more anticancer drugs may be administered at time intervals.

The anticancer drug may include, but is not limited to, conventional anticancer drugs or targeted anticancer drugs that attack only cancer cells through molecular targets specific to respective cancer types (in which cancer growth and metastasis are caused by activity of specific molecules involved in cancer growth and carcinogenesis).

The conventional anticancer drug may be at least one selected from the group consisting of adriamycin, amsacrine, bleomycin, busulphan, cyclophosphamide, cytarabine, daunorubicin, docetaxel, epirubicin, etoposide, 5-fluorouracil, gemcitabine, ifosfamide, irinotecan, lomustine, melphalan, paclitaxel, thiotepa, topotecan, vinblastine, vindesine, and vinorelbine, and may preferably be at least one selected from the group consisting of docetaxel, adriamycin, and cyclophosphamide.

The compound may be dependent on the enzyme NAD(P)H: quinone oxidoreductase 1 (NQO1).

The compound can suppress falling-off of hair follicles and inner root sheaths.

In a specific embodiment of the present invention, the present inventors established an animal model having chemotherapy-induced alopecia by a single intraperitoneal injection of cyclophosphamide into C57BL/6 mice. The animal model was orally administered dunnione on a daily basis starting from 3 days prior to cyclophosphamide administration. As a result, it was identified that the cyclophosphamide plus dunnione combination-treated group exhibits inhibited hair loss (FIGS. 2a to 3c), and suppressed falling-off of hair follicles and inner root sheaths in the skin tissue and increased number of hairs (FIG. 4), as compared with the cyclophosphamide alone-treated group.

Figure 7:
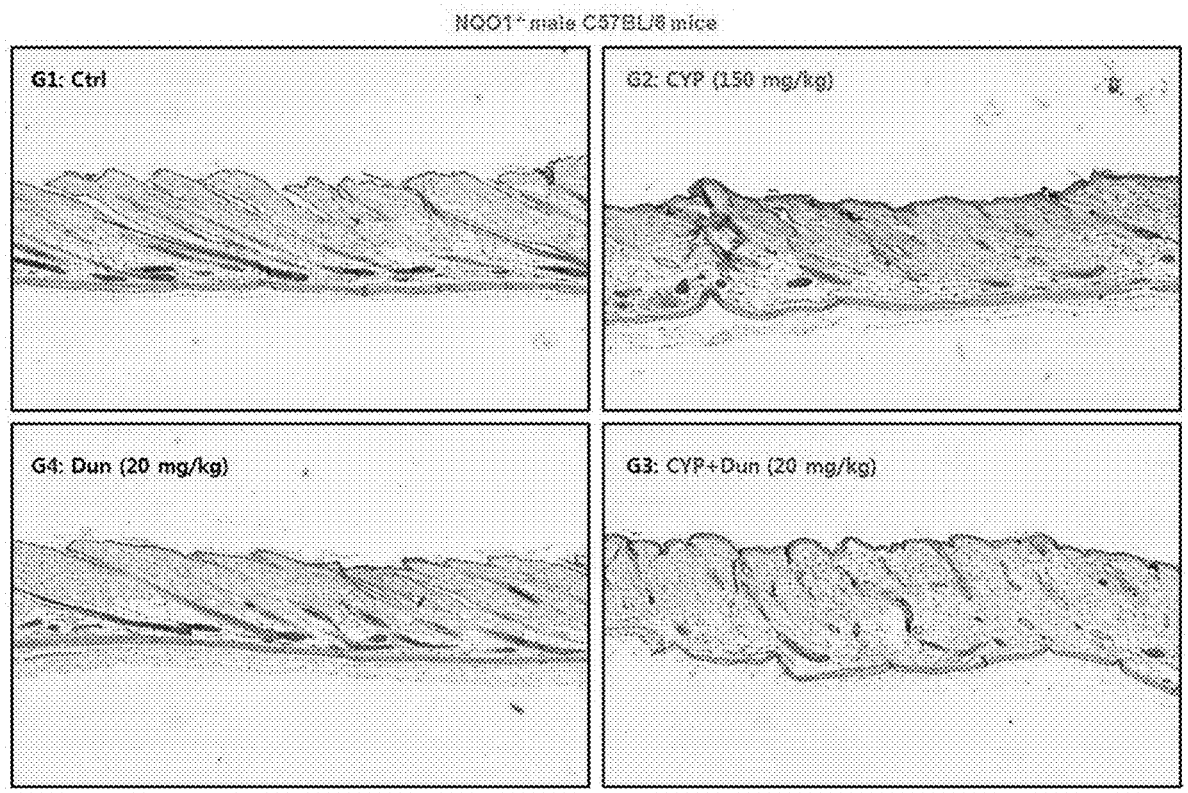
FIG. 7 illustrates results obtained by observing, with an optical microscope, the mouse skin surface on day 18 after hair removal in the NQO1 knockout mice: G1: Ctrl (PBS-treated group); G2: CYP (cyclophosphamide-treated group); G3: CYP+Dun (cyclophosphamide plus dunnione combination-treated group); G4: Dun (dunnione alone-treated group).

In addition, in order to identify whether a hair loss inhibitory effect of dunnione is mediated by the enzyme NAD(P)H: quinone oxidoreductase 1 (NQO1), the present inventors established an NQO1 knockout animal model having chemotherapy-induced alopecia by a single intraperitoneal injection of cyclophosphamide into NQO1 knockout mice. The animal model was orally administered dunnione on a daily basis starting from 3 days prior to cyclophosphamide administration. As a result, it was identified with gross examination that unlike the results seen with the C57BL/6 mice, the cyclophosphamide plus dunnione combination-treated group exhibits progression of hair loss to a level similar to the cyclophosphamide alone-treated group (FIGS. 5a to 6b); and it was identified that falling-off of hair follicles and inner root sheaths in the skin tissue progresses in the cyclophosphamide plus dunnione combination-treated group (FIG. 7).

In addition, in order to identify whether dunnione leads to increased $NAD^+$ concentration and increased activity of the enzyme Sirt1, the present inventors analyzed $NAD^+$ and NADH concentrations and $NAD^+$/NADH ratio in the skin tissue obtained on day 18 after hair removal in a mouse model having cyclophosphamide-induced alopecia. As a result, a phenomenon was observed in which dunnione increases the expression level of Sirt1 protein, the $NAD^+$ concentration, and the $NAD^+$/NADH ratio which have been decreased by cyclophosphamide (FIGS. 8a to 8c); and it was identified that in the cyclophosphamide plus dunnione combination-treated group, activity of the Sirt1 protein, which uses $NAD^+$ as a substrate, is maintained at a level similar to the normal group (FIG. 8d). In addition, a phenomenon was observed in which although cyclophosphamide has lead to decreased expression of Sirt1 protein and increased acetylation of the target proteins, NF-κB p65 and p53, in the skin tissue, combined treatment with dunnione normalizes Sirt1 expression and suppresses acetylation reaction of p65 and p53 (FIG. 9).

In addition, the present inventors established an animal model having chemotherapy-induced alopecia by combined administration of docetaxel, adriamycin, and cyclophosphamide (hereinafter designated as TAC) in C57BL/6 mice. The animal model was orally administered dunnione on a daily basis starting from 3 days prior to TAC administration. As a result, it was identified that the TAC plus dunnione combination-treated group exhibits inhibited hair loss (FIGS. 11a to 12b), and suppressed falling-off of hair follicles and inner root sheaths in the skin tissue and increased number of hairs (FIG. 13), as compared with the TAC alone-treated group.

Figure 14:
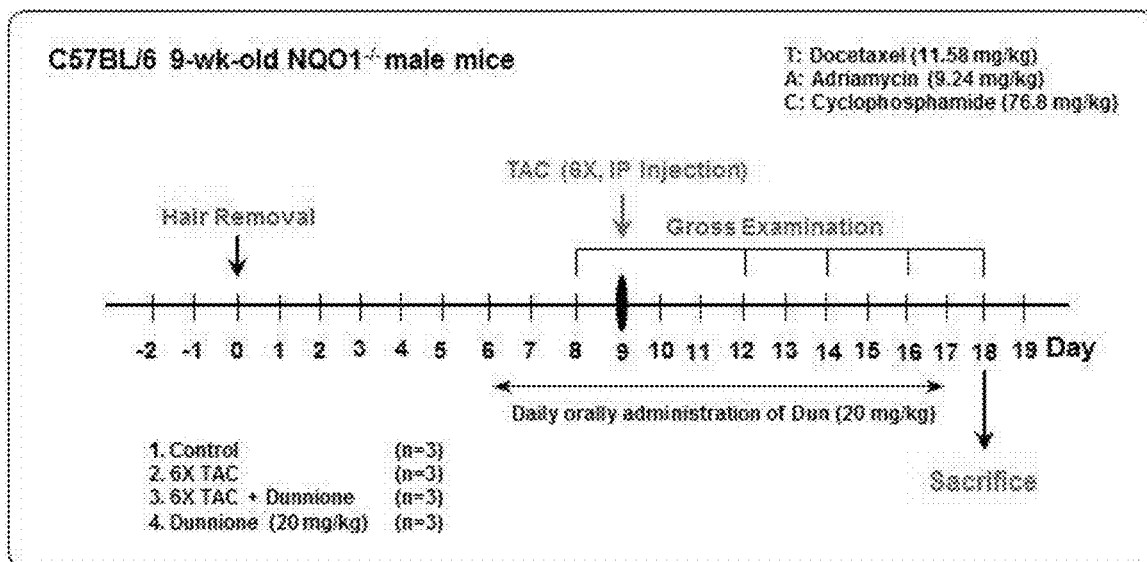
FIG. 14 illustrates an experimental plan for identifying a hair loss inhibitory effect of dunnione in an NQO1 knockout animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione (20 mg/kg) alone-treated group).
Figure 15:
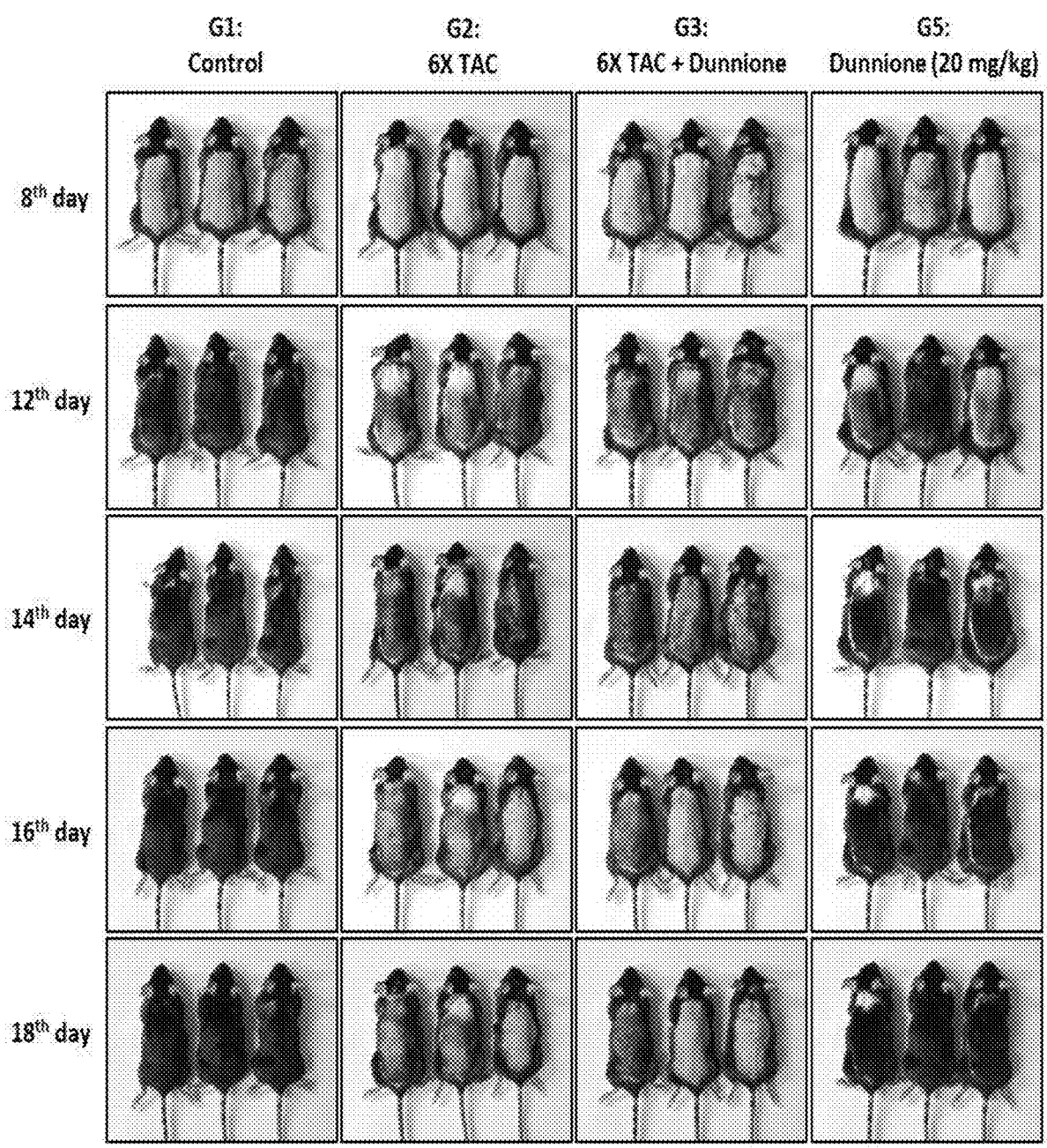
FIG. 15 illustrates results obtained by taking photographs of the mouse skin surface on days 8, 12, 14, 16, and 18 after hair removal in the NQO1 knockout animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).
Figure 16:
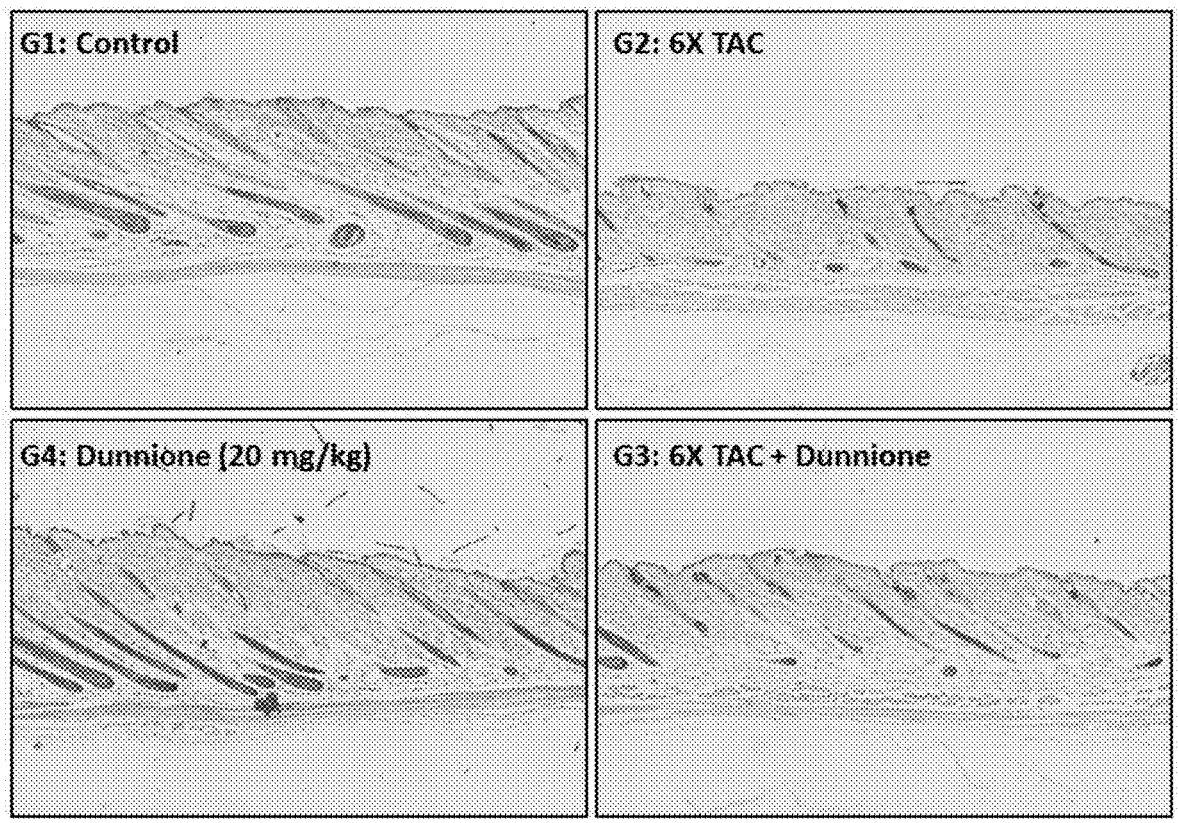
FIG. 16 illustrates results obtained by observing, with an optical microscope, the mouse skin surface on day 18 after hair removal in the NQO1 knockout animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).

In order to identify whether a hair loss inhibitory effect of dunnione is mediated by the enzyme NAD(P)H: quinone oxidoreductase 1 (NQO1), the present inventors established an NQO1 knockout animal model having chemotherapy-induced alopecia by intraperitoneal injection of the combined anticancer drug TAC into NQO1 knockout mice (FIG. 14). The animal model was orally administered dunnione on a daily basis starting from 3 days prior to TAC administration. As a result, it was identified with gross examination that unlike the results seen with the C57BL/6 mice, the TAC plus dunnione combination-treated group exhibits progression of hair loss to a level similar to the TAC alone-treated group (FIG. 15); and it was identified that falling-off of hair follicles and inner root sheaths in the skin tissue progresses in the TAC plus dunnione combination-treated group (FIG. 16).

From these results, it was identified that the dunnione compound of the present invention inhibits hair loss and suppresses falling-off of hair follicles and inner root sheaths, in an NQO1-dependent manner, in an animal model having alopecia caused by administration of cyclophosphamide alone or an animal model having alopecia caused by combined administration of docetaxel, adriamycin, and cyclophosphamide. Accordingly, the dunnione compound of the present invention, a pharmaceutically acceptable salt thereof, a prodrug thereof, a solvate thereof, or an isomer thereof can be effectively used as an active ingredient in a pharmaceutical composition for prevention or amelioration of chemotherapy-induced alopecia.

In another aspect of the present invention, there is provided a composition for promoting hair growth, comprising, as an active ingredient, a compound represented by Formula 1, a pharmaceutically acceptable salt thereof, a prodrug thereof, a solvate thereof, or an isomer thereof:

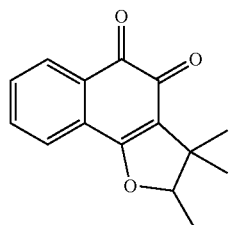

[Formula 1]

In yet another aspect of the present invention, there is provided a use of the pharmaceutical composition of the present invention for preventing or ameliorating hair loss.

In still yet another aspect of the present invention, there is provided a use of the pharmaceutical composition of the present invention for manufacturing a medicament for prevention or treatment of hair loss.

In still yet another aspect of the present invention, there is provided a method for preventing or ameliorating hair loss, comprising a step of applying the pharmaceutical composition of the present invention.

MODE FOR THE INVENTION

Hereinafter, the present invention will be described in detail by way of the following examples. However, the following examples are merely given to illustrate the present invention, and the scope of the present invention is not limited by the following examples.

Example 1. Preparation of Animal Model in which Hair Follicles at New Anagen Phase are Induced All mice used in experiments were kept in germ-free animal facility where constant temperature (22° C. to 26° C.) and constant humidity (55% to 60%) are maintained. The mice were acclimatized for one week with access to sufficient water and normal solid feed (SAMTAKO Bio Korea Co., Ltd., Korea), and then used for experiments. All experiments were conducted, under approval from the Institutional Animal Care and Use Committee of Wonkwang University, in compliance with the Committee's guidelines for the care and ethics of laboratory animals.

In 9-week-old C57BL/6 mice, the hair on the dorsal skin area was first removed with an animal hair clipper, and then a depilatory (Niclean cream, manufactured by Ildong Pharmaceutical Co., Ltd.) was applied to the dorsal skin to completely remove the hair. The remaining depilatory was washed with running water so that hair follicles at a new anagen phase are induced, the hair follicles being distinguished from hair follicles at an anagen phase which are spontaneously induced.

Example 2. Experimental Groups for Identifying Hair Loss Inhibitory Effect of Dunnione in Animal Model Having Alopecia Caused by Cyclophosphamide In order to identify a hair loss inhibitory effect of dunnione in an animal model having chemotherapy-induced alopecia (CIA), animals were divided into four experimental groups and used for experiments. As an anticancer drug, cyclophosphamide (hereinafter designated as CYP) was used.

The day, on which the mice were hair-removed in Example 1, was set as day 0, and the animals were divided into the following groups: normal group (Control, 4 animals) in which only PBS is intraperitoneally injected on day 9; cyclophosphamide group (CYP, 6 animals) in which cyclophosphamide (150 mg/kg) is intraperitoneally injected on day 9; combination-treated group (CYP+Dunnione, 6 animals) in which dunnione is orally administered on a daily basis starting from 3 days prior to treatment with cyclophosphamide; and dunnione alone-treated group (Dunnione, 4 animals) in which only dunnione (20 mg/kg) is administered (FIG. 1).

Experimental Example 1. Visual Observation of Skin in Animal Model Having Alopecia Caused by Cyclophosphamide, Following Treatment with Dunnione The day, on which the mice were hair-removed in Example 1, was set as day 0; and hair growth-related visual characteristics, which are observed on the animal's skin in each of the experimental groups described in Example 2, were photographed using a digital camera on days 8, 12, 14, 16, and 18.

Figure 2A:
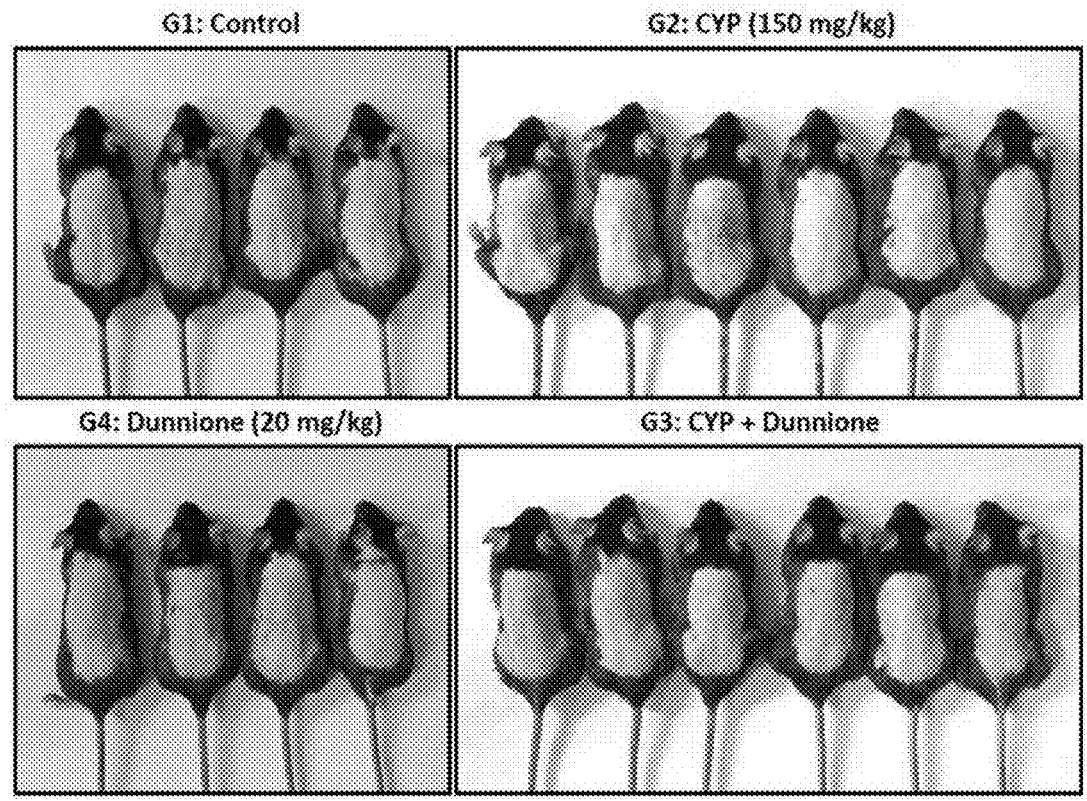
FIG. 2a illustrates results obtained by taking photographs of the skin surface for respective experimental groups on day 8 after hair removal in the animal model having alopecia caused by cyclophosphamide: G1: Control (PBS-treated group); G2: CYP (cyclophosphamide-treated group); G3: CYP+Dunnione (cyclophosphamide plus dunnione combination-treated group); G4: Dunnione (dunnione alone-treated group).
Figure 2B:
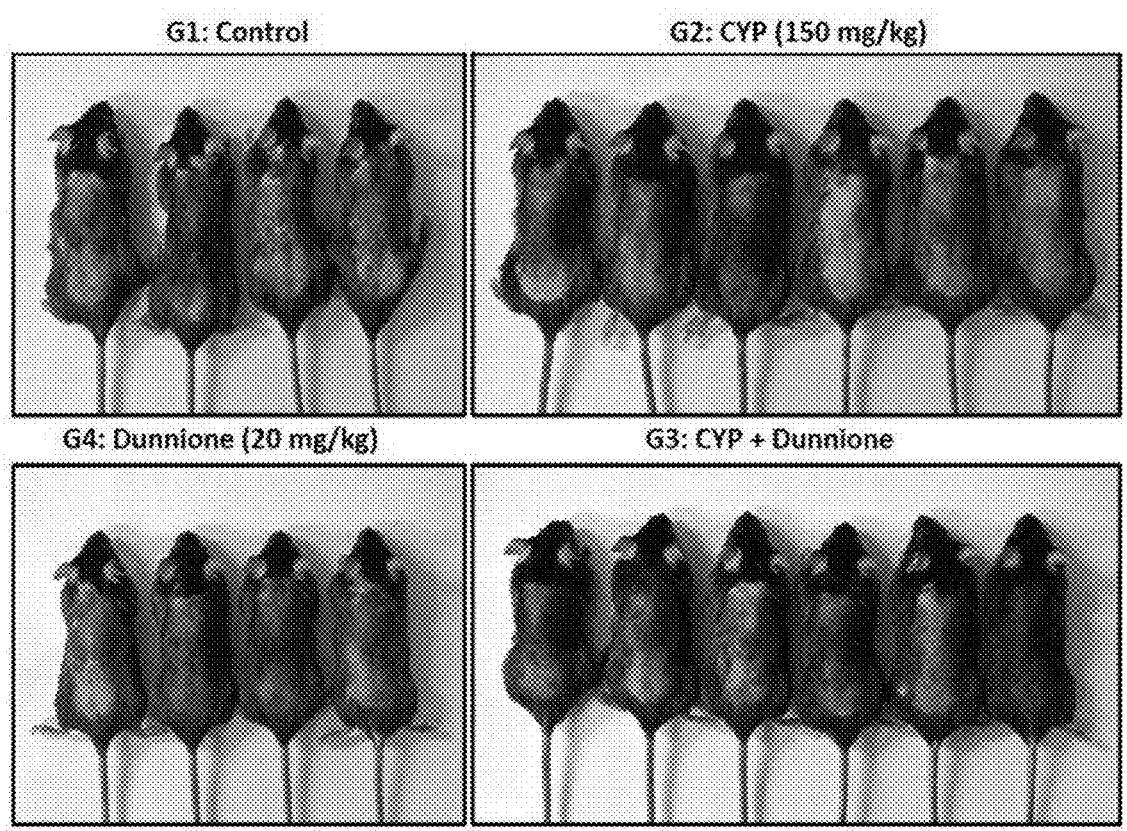
FIG. 2b illustrates results obtained by taking photographs of the skin surface for respective experimental groups on day 12 after hair removal in the animal model having alopecia caused by cyclophosphamide: G1: Control (PBS-treated group); G2: CYP (cyclophosphamide-treated group); G3: CYP+Dunnione (cyclophosphamide plus dunnione combination-treated group); G4: Dunnione (dunnione alone-treated group).

In all experimental groups in Example 2, hair hardly grew until day 8 after hair removal (FIG. 2a). On day 12 after hair removal, hair began to grow in a similar pattern in all experimental groups (FIG. 2b).

Figure 3A:
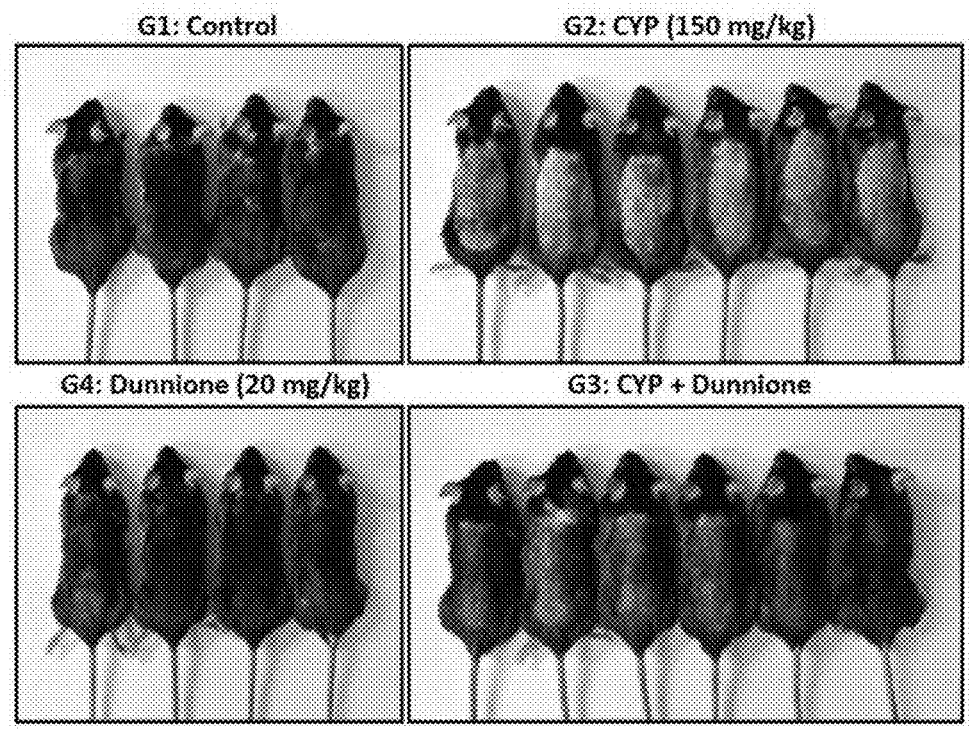
FIG. 3a illustrates results obtained by taking photographs of the skin surface for respective experimental groups on day 14 after hair removal in the animal model having alopecia caused by cyclophosphamide: G1: Control (PBS-treated group); G2: CYP (cyclophosphamide-treated group); G3: CYP+Dunnione (cyclophosphamide plus dunnione combination-treated group); G4: Dunnione (dunnione alone-treated group).
Figure 3B:
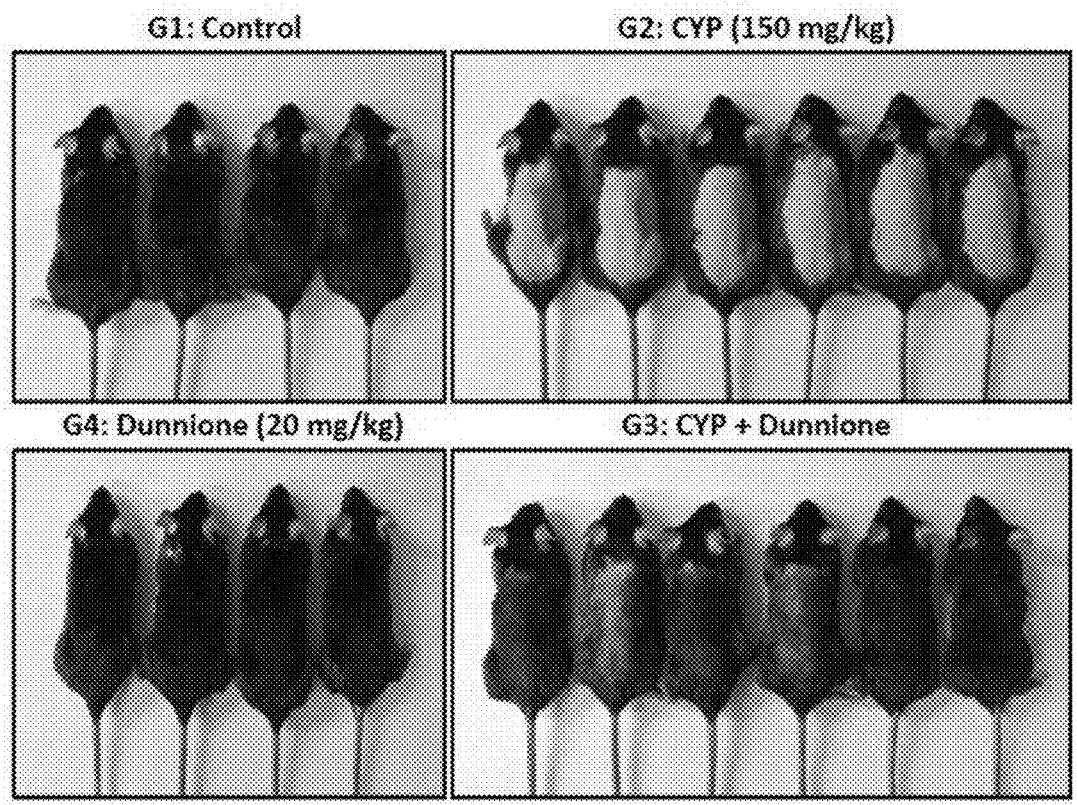
FIG. 3b illustrates results obtained by taking photographs of the skin surface for respective experimental groups on day 16 after hair removal in the animal model having alopecia caused by cyclophosphamide: G1: Control (PBS-treated group); G2: CYP (cyclophosphamide-treated group); G3: CYP+Dunnione (cyclophosphamide plus dunnione combination-treated group); G4: Dunnione (dunnione alone-treated group).
Figure 3C:
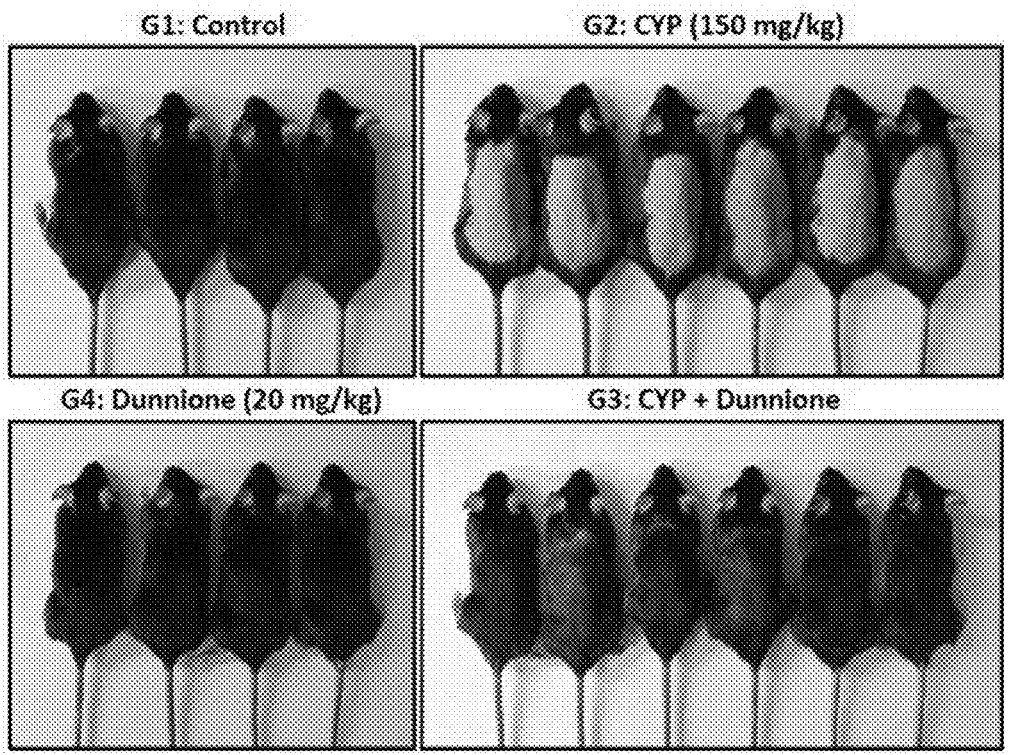
FIG. 3c illustrates results obtained by taking photographs of the skin surface for respective experimental groups on day 18 after hair removal in the animal model having alopecia caused by cyclophosphamide: G1: Control (PBS-treated group); G2: CYP (cyclophosphamide-treated group); G3: CYP+Dunnione (cyclophosphamide plus dunnione combination-treated group); G4: Dunnione (dunnione alone-treated group).

On day 14 after hair removal, the dunnione plus cyclophosphamide combination-treated group (CYP+Dunnione) began to grow more hair than the cyclophosphamide alone-treated group (CYP); and on day 18 after hair removal, in all experimental groups, except for the cyclophosphamide alone-treated group, hair grew overall so that the skin is full of hair and looks black (FIGS. 3a to 3c).

Experimental Example 2. Observation of Histological Changes in Skin in Animal Model Having Alopecia Caused by Cyclophosphamide, Following Treatment with Dunnione The day, on which the mice were hair-removed in Example 1, was set as day 0, and the mice in each of the experimental groups described in Example 2 were sacrificed on day 18. Subsequently, the mouse dorsal skin was dissected parallel or perpendicular to the vertebral line, and removed. The removed skin was fixed with a Bouin's solution for 12 hours, subjected to dehydration, and embedded in paraffin. Then, the resulting product was prepared into 5-μm sections. The prepared sections were subjected to hematoxylin and eosin (H&E) staining, and histological changes in the skin in each experimental group were observed.

Figure 4:
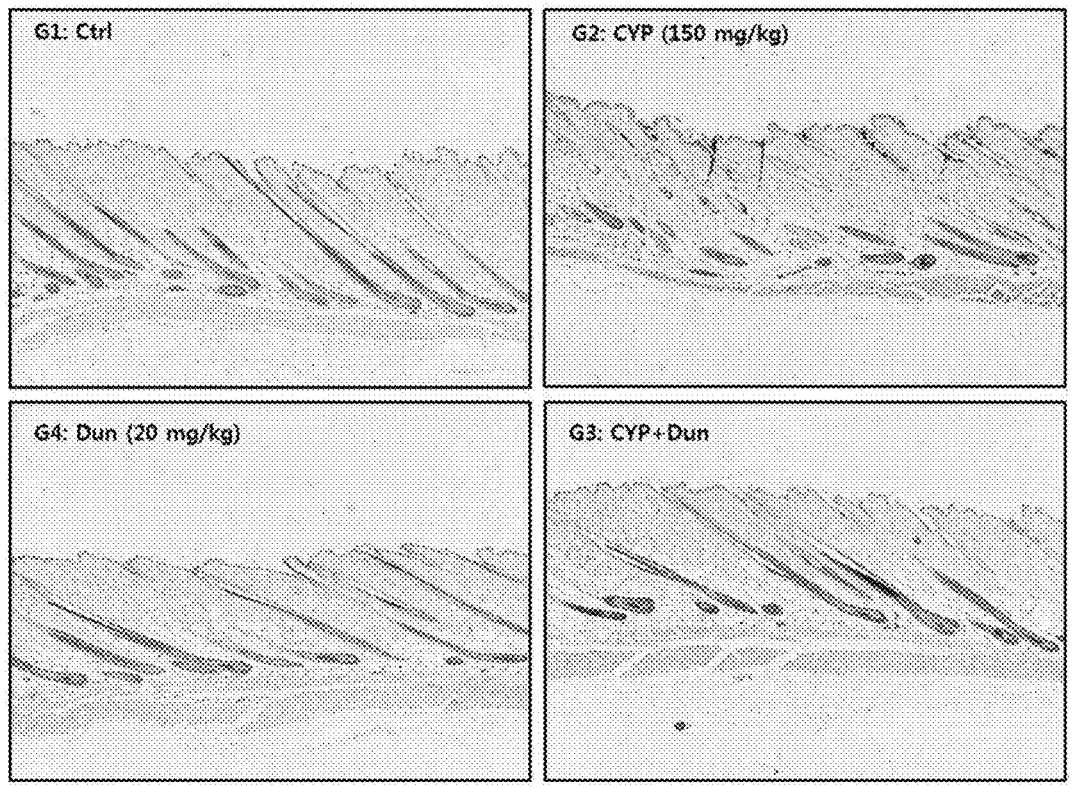
FIG. 4 illustrates results obtained by observing, with an optical microscope, the mouse skin surface on day 18 after hair removal in the animal model having alopecia caused by cyclophosphamide: G1: Ctrl (PBS-treated group); G2: CYP (cyclophosphamide-treated group); G3: CYP+Dun (cyclophosphamide plus dunnione combination-treated group); G4: Dun (dunnione alone-treated group).
Figure 5A:
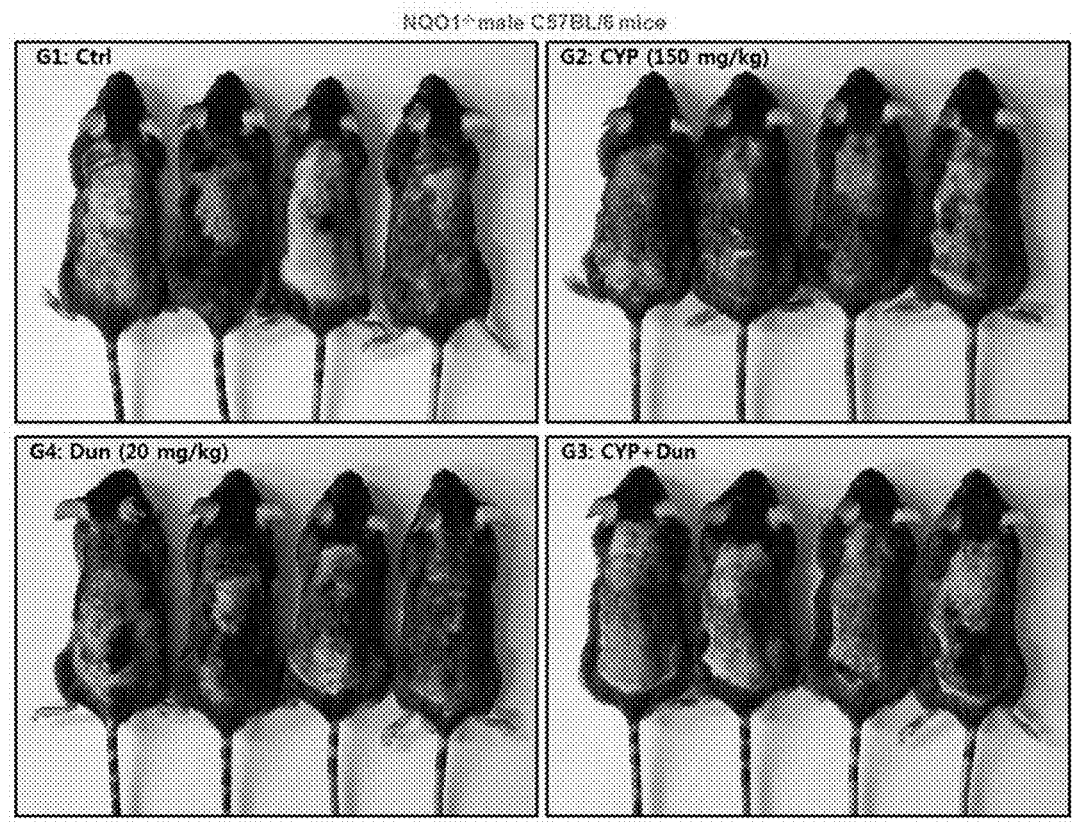
FIG. 5a illustrates results obtained by taking photographs of the skin surface for respective experimental groups on day 12 after hair removal in NQO1 knockout mice: G1: Ctrl (PBS-treated group); G2: CYP (cyclophosphamide-treated group); G3: CYP+Dun (cyclophosphamide plus dunnione combination-treated group); G4: Dun (dunnione alone-treated group).
Figure 5B:
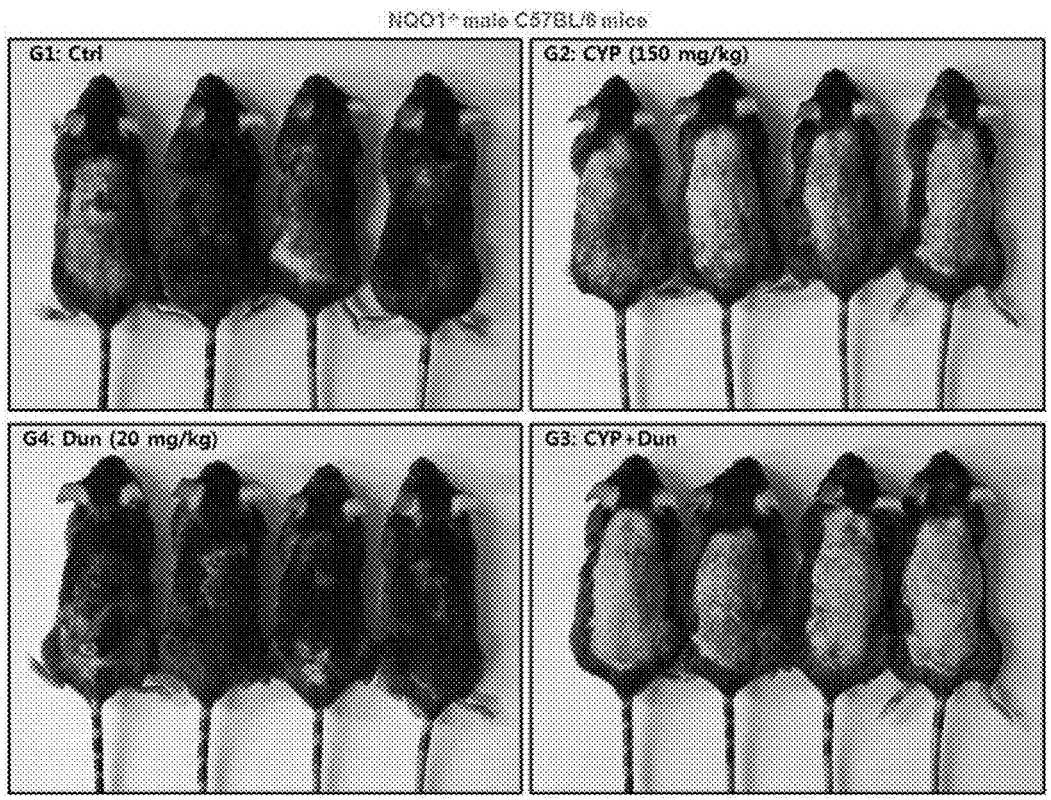
FIG. 5b illustrates results obtained by taking photographs of the skin surface for respective experimental groups on day 14 after hair removal in NQO1 knockout mice: G1: Ctrl (PBS-treated group); G2: CYP (cyclophosphamide-treated group); G3: CYP+Dun (cyclophosphamide plus dunnione combination-treated group); G4: Dun (dunnione alone-treated group).
Figure 6A:
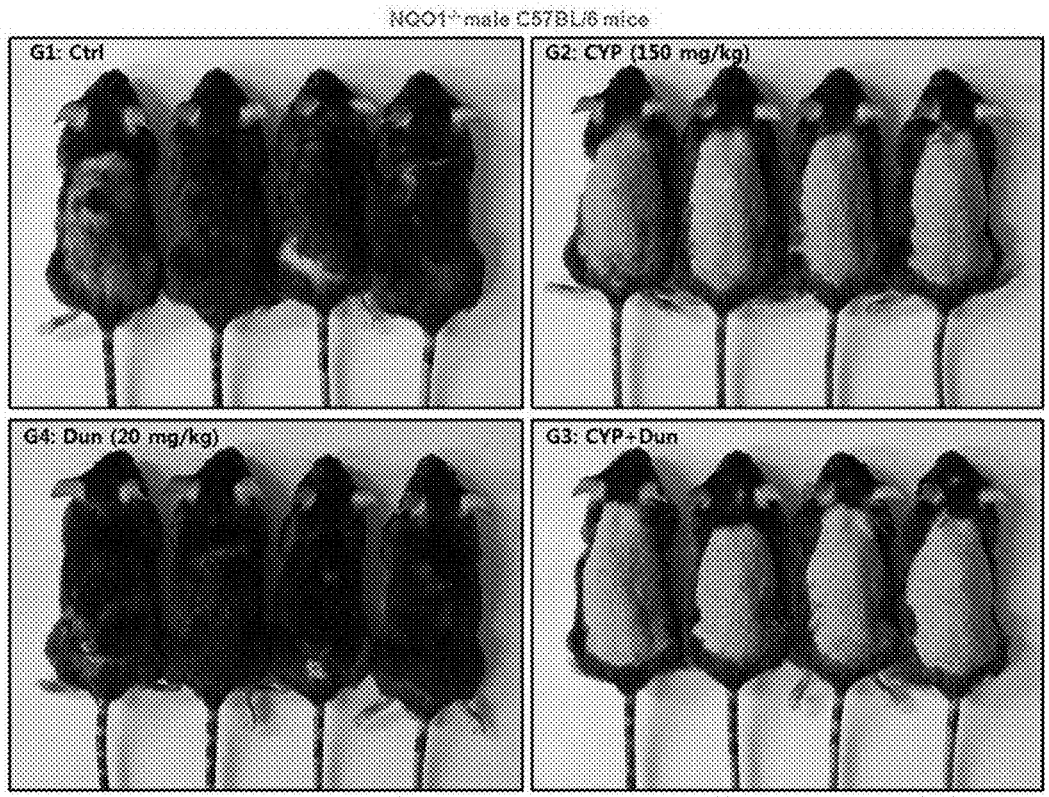
FIG. 6a illustrates results obtained by taking photographs of the skin surface for respective experimental groups on day 16 after hair removal in NQO1 knockout mice: G1: Ctrl (PBS-treated group); G2: CYP (cyclophosphamide-treated group); G3: CYP+Dun (cyclophosphamide plus dunnione combination-treated group); G4: Dun (dunnione alone-treated group).
Figure 6B:
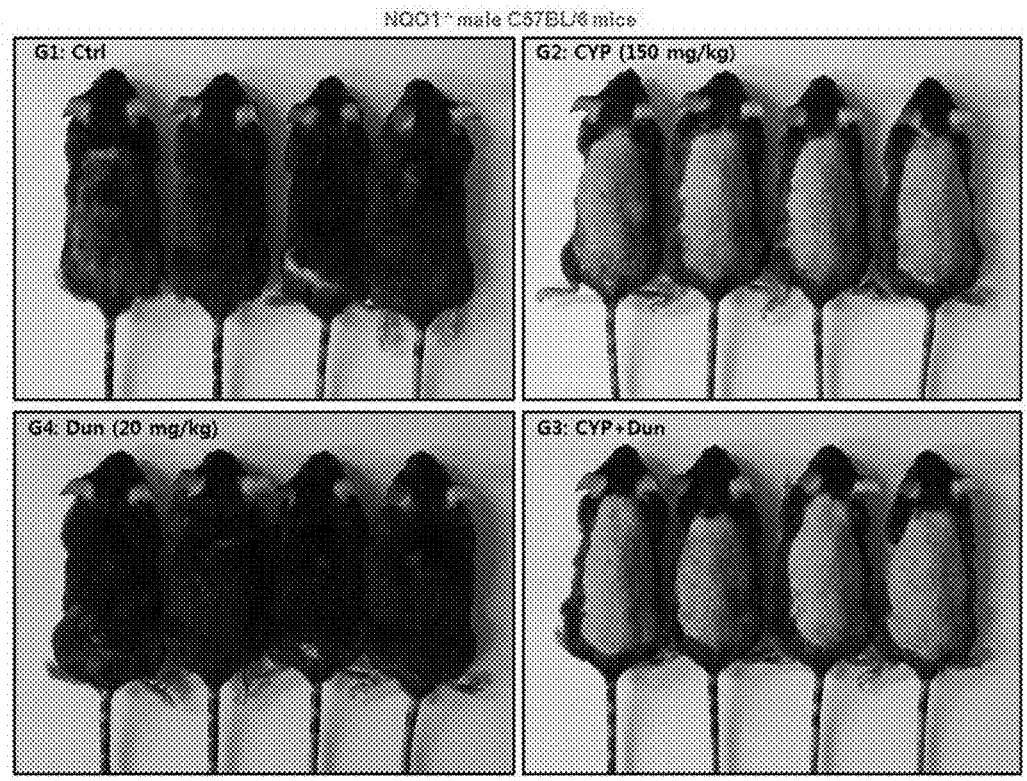
FIG. 6b illustrates results obtained by taking photographs of the skin surface for respective experimental groups on day 18 after hair removal in NQO1 knockout mice: G1: Ctrl (PBS-treated group); G2: CYP (cyclophosphamide-treated group); G3: CYP+Dun (cyclophosphamide plus dunnione combination-treated group); G4: Dun (dunnione alone-treated group).

As a result, it was observed that in the cyclophosphamide alone-treated group (CYP), overall, the hair follicles have poorly developed or the inner root sheaths have insufficiently developed, whereas it was observable that in the cyclophosphamide plus dunnione combination-treated group (CYP+Dun), the hair follicles and the inner root sheaths have well developed overall, and the number of growing hairs has increased as compared with the cyclophosphamide alone-treated group (FIG. 4).

Example 3. Relationship Between Hair Loss Inhibitory Effect of Dunnione and Enzyme NQO1

In order to identify whether a hair loss inhibitory effect of dunnione in an animal model having chemotherapy-induced alopecia (CIA) is dependent on the enzyme NQO1, the same experiments as described in Examples 1 and 2 were repeatedly performed using NAD(P)H: quinone oxidoreductase 1 (NQO1) knockout mice in place of the C57BL/6 mice.

The day, on which the NQO1 knockout mice were hair-removed according to Example 1, was set as day 0, and the animals were divided into the following experimental groups and used for experiments: normal group (Control, 4 animals) in which only PBS is intraperitoneally injected on day 9; cyclophosphamide group (CYP, 6 animals) in which cyclophosphamide (150 mg/kg) is intraperitoneally injected on day 9; combination-treated group (CYP+Dunnione, 6 animals) in which dunnione is orally administered on a daily basis starting from 3 days prior to treatment with cyclophosphamide; and dunnione alone-treated group (Dunnione, 4 animals) in which only dunnione (20 mg/kg) is administered (FIG. 1).

Experimental Example 3. Visual Observation of Skin in NQO1 Knockout Mice, Following Treatment with Dunnione The day, on which the NQO1 knockout mice were hair-removed according to Example 1, was set as day 0; and hair growth-related visual characteristics, which are observed on the animal's skin in each of the experimental groups described in Example 3, were photographed using a digital camera on days 12, 14, 16, and 18.

For the normal group (Ctrl) injected with only PBS and the dunnione alone-treated group (Dun) in Example 3, hair began to grow starting from day 12 after hair removal (FIG. 5a) and hair grew overall on day 18 so that the skin is full of hair and looks black (FIG. 6b), similar to the results seen with the C57BL/6 mice. On the other hand, for the cyclophosphamide alone-treated group (CYP) and the dunnione plus cyclophosphamide combination-treated group (CYP+Dun), hair hardly grew until day 18 after hair removal (FIGS. 5a to 6b).

Experimental Example 4. Observation of Histological Changes in Skin in NQO1 Knockout Mice, Following Treatment with Dunnione The day, on which the NQO1 knockout mice were hair-removed according to Example 1, was set as day 0, and the mice in each of the experimental groups described in Example 3 were sacrificed on day 18. Subsequently, the mouse dorsal skin was dissected parallel or perpendicular to the vertebral line, and removed. The removed skin was fixed with a Bouin's solution for 12 hours, subjected to dehydration, and embedded in paraffin. Then, the resulting product was prepared into 5-μm sections. The prepared sections were subjected to hematoxylin and eosin (H&E) staining, and histological changes in the skin in each experimental group were observed.

The histological observations showed that in the normal group (Ctrl) injected with only PBS and the dunnione alone-treated group (Dun), the hair follicles and inner root sheaths have well developed overall, similar to the results seen with the C57BL/6 mice, whereas in the cyclophosphamide alone-treated group (CYP) and the dunnione plus cyclophosphamide combination-treated group (CYP+Dun), overall, the hair follicles have poorly developed or the inner root sheaths have insufficiently developed (FIG. 7).

Experimental Example 5. Identification of Increased $NAD^+$ Concentration and Increased Enzyme Activity of Sirt1 in Normal Mice, Following Treatment with Dunnione In the mouse model having alopecia caused by cyclophosphamide of Example 2, analysis of $NAD^+$ and NADH concentrations, $NAD^+$/NADH ratio, and Sirt1 protein activity was performed on the skin tissue obtained on day 18 after hair removal.

Specifically, in order to quantify the $NAD^+$ and NADH concentrations in the skin tissue obtained from the animal model prepared by the method in Example 2, the skin tissue was tested with the analysis kit (E2ND-100) of BioAssay Systems according to the instruction manual, and then the $NAD^+$/NADH ratio was analyzed. First, 10 mg of skin tissue was collected from the animal model. Then, 100 μl of extraction solution for $NAD^+$ or NADH was added to the skin tissue and homogenized. Then, the homogenized skin tissue was subjected to heat treatment at 60° C. for 5 minutes. Neutralization was performed by addition of the same volume of the extraction solution, and then centrifugation was performed at 14,000 rpm for 5 minutes to obtain the supernatant. Then, a developing reagent was added to the supernatant. The $NAD^+$ and NADH concentrations were determined from the absorbance measured at a wavelength of 565 nm, and the $NAD^+$/NADH ratio was analyzed.

Figure 8A:
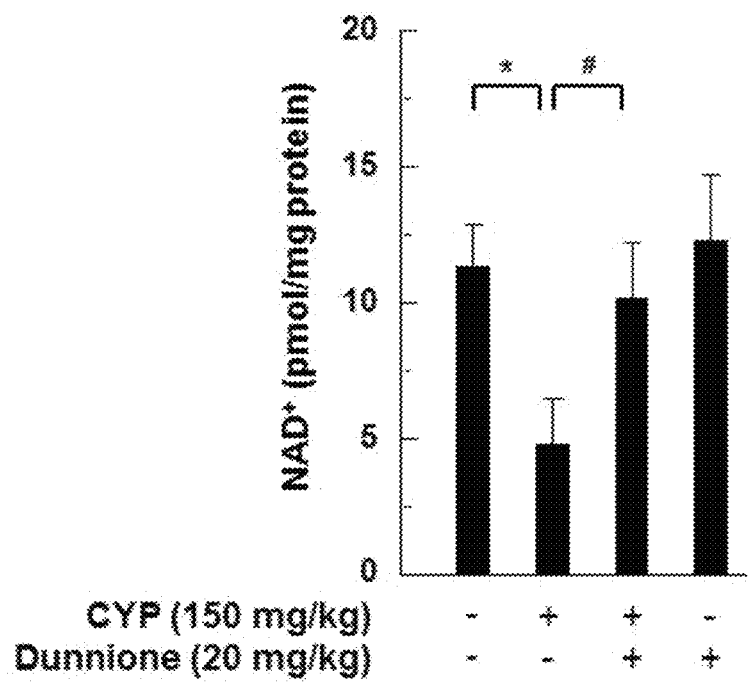
FIG. 8a illustrates a diagram showing the $NAD^+$ concentration in skin tissue in the presence or absence of treatment with dunnione in the animal model having alopecia caused by cyclophosphamide (*$p<0.05$: comparison being made between the normal group and the cyclophosphamide group, #$p<0.05$: comparison being made between the cyclophosphamide group and the cyclophosphamide+dunnione combination-treated group).
Figure 8B:
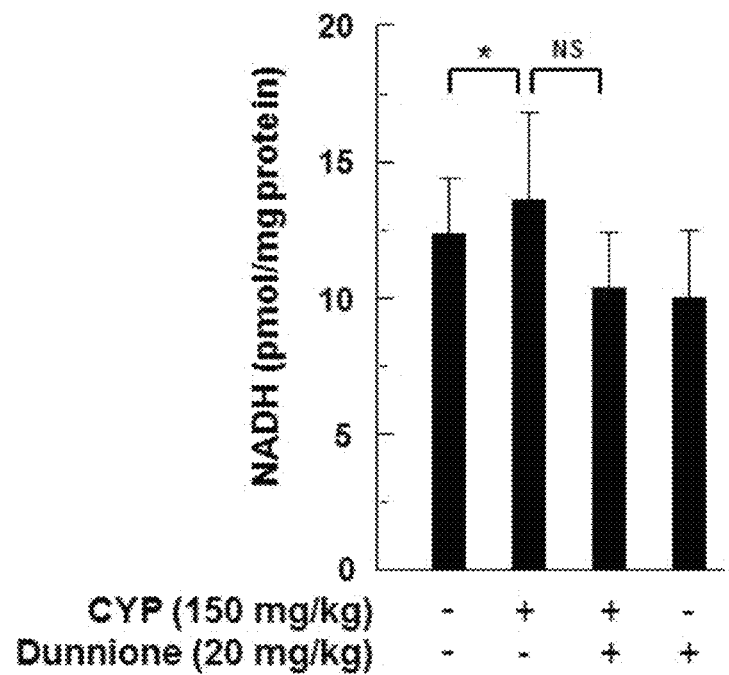
FIG. 8b illustrates a diagram showing the NADH concentration in skin tissue in the presence or absence of treatment with dunnione in the animal model having alopecia caused by cyclophosphamide (*$p<0.05$: comparison being made between the normal group and the cyclophosphamide group).
Figure 8C:
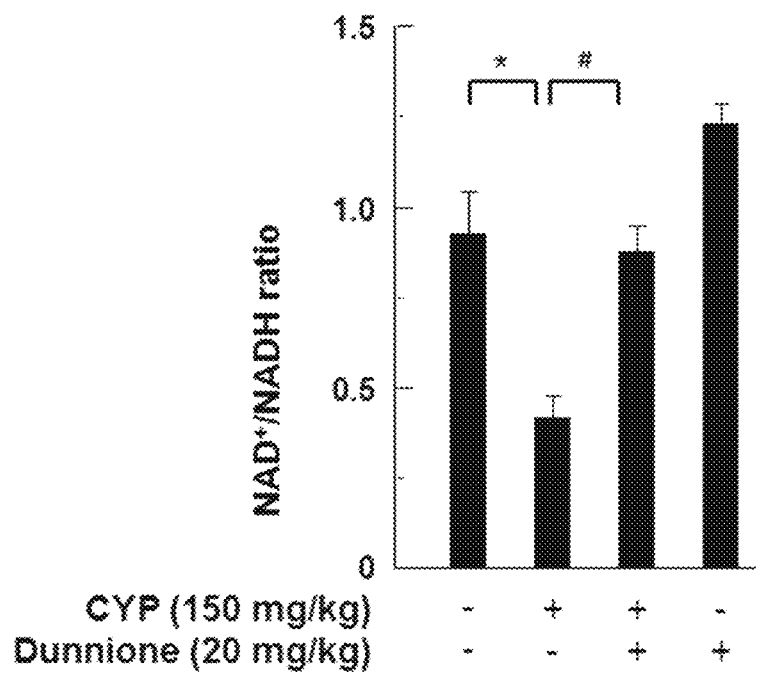
FIG. 8c illustrates a diagram showing the $NAD^+$/NADH ratio in skin tissue in the presence or absence of treatment with dunnione in the animal model having alopecia caused by cyclophosphamide (*$p<0.05$: comparison being made between the normal group and the cyclophosphamide group, #$p<0.05$: comparison being made between the cyclophosphamide group and the cyclophosphamide plus dunnione combination-treated group).
Figure 8D:
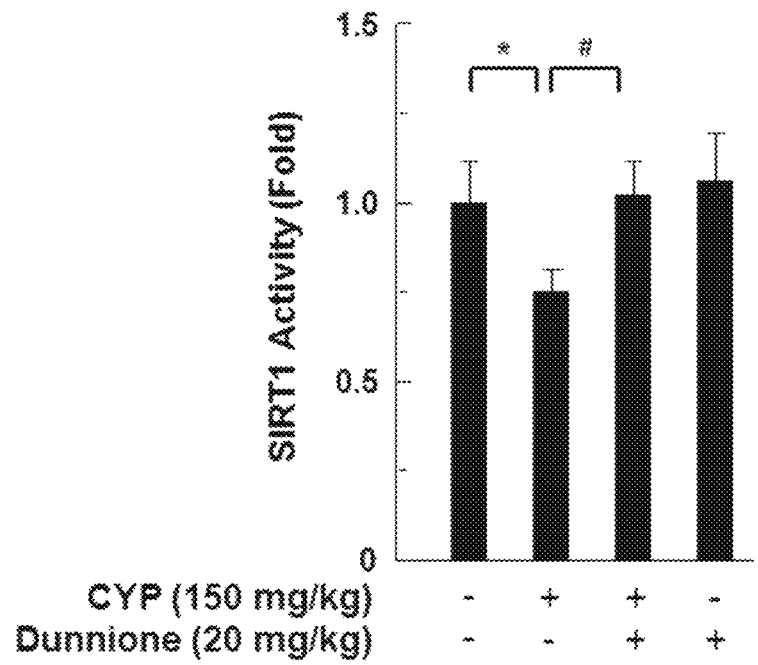
FIG. 8d illustrates a diagram showing the Sirt1 activity in skin tissue in the presence or absence of treatment with dunnione in the animal model having alopecia caused by cyclophosphamide (*$p<0.05$: comparison being made between the normal group and the cyclophosphamide group, #$p<0.05$: comparison being made between the cyclophosphamide group and the cyclophosphamide plus dunnione combination-treated group).
Figure 9:
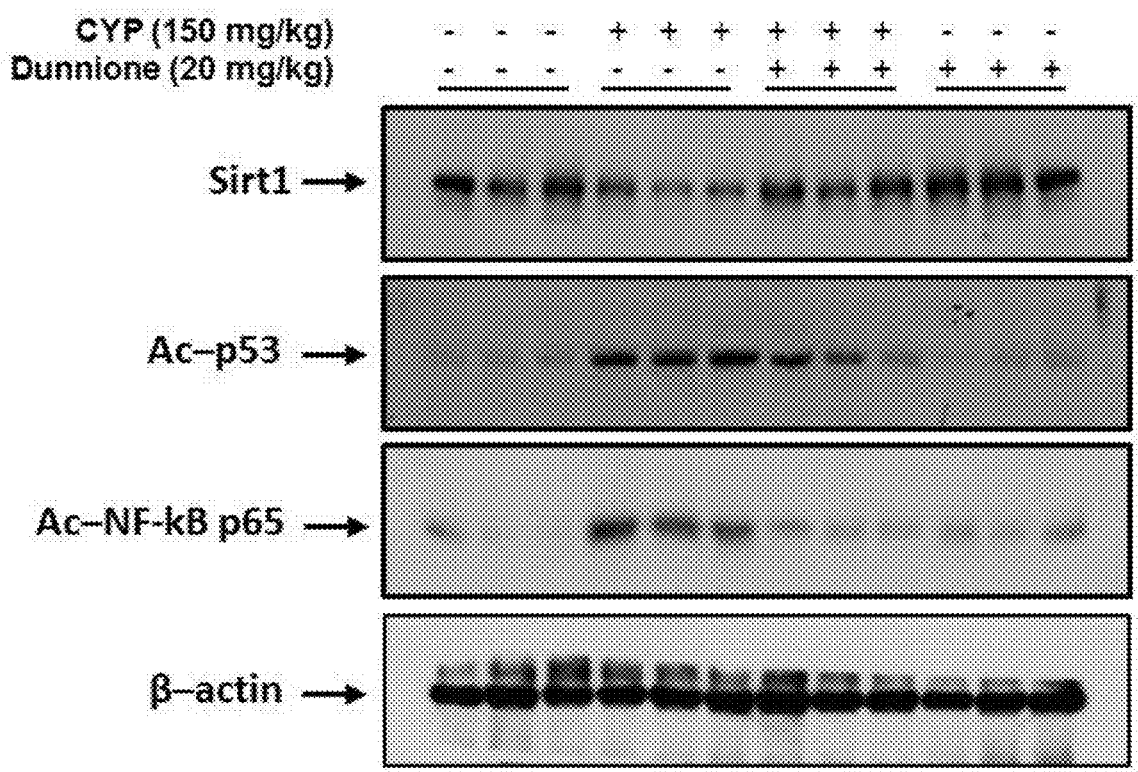
FIG. 9 illustrates a diagram showing an effect of dunnione on expression of Sirt1 protein and acetylation of p65 and p53 proteins in skin tissue in the animal model having alopecia caused by cyclophosphamide.

As a result, a phenomenon was observed in which dunnione increases the expression level of Sirt1 protein, the $NAD^+$ concentration, and the $NAD^+$/NADH ratio which have been decreased by cyclophosphamide (FIGS. 8a to 8c).

In addition, the skin tissue obtained from the animal model prepared by the method in Example 2 was homogenized. The homogenized skin tissue was tested with the fluorescent Sirt1 detection kit (BML-AK555-0001) of Enzo Life Sciences International, Inc. according to the instruction manual, and then Sirt1 activity was analyzed. 40 μg of the homogenized skin tissue was mixed with a reaction solution (Fluor de Lys-Sirt1, NAD+, buffer solution (25 mM Tris-HCl (pH8.0), 137 mM NaCl, 2.7 mM LCl, 1 mM $MgCl_2$, and 1 mg/mL BSA)), and reaction was allowed to proceed at a temperature of 37° C. for 1 hour. Then, additional reaction was allowed to proceed for 5 minutes under a condition in which a developer is added. In order to check the final Sirt1 activity, readings were measured for the reaction solution using the CytoFluor series 4000 fluorometer (PerSeptive Biosystems, Inc., USA) with the excitation wavelength set to 360 nm and the emission to 460 nm.

As a result, it was identified that activity of the Sirt1 protein, which uses $NAD^+$ as a substrate, is decreased by cyclophosphamide. On the other hand, it was identified that in the cyclophosphamide plus dunnione combination-treated group, activity of the Sirt1 protein is maintained at a level similar to the normal group (FIG. 8d).

Experimental Example 6. Identification of Acetylation Reaction of Target Proteins of Sirt1, Following Treatment with Dunnione In the cyclophosphamide-induced alopecia mouse model of Example 2, expression level of Sirt1 protein and acetylation reaction of the target proteins thereof, NF-κB p65 and p53, were identified on the skin tissue obtained on day 18 after hair removal.

Specifically, 10 mg of the skin tissue obtained from the animal model prepared by the method in Example 2 was homogenized by addition of a lysis solution (RIPA lysis buffer). Then, centrifugation was performed at 14,000 rpm for 10 minutes. The protein concentration in the supernatant was quantified with a bovine serum albumin (BSA) standard solution. The skin tissue protein was used in an amount of 40 μg per test solution. First, the homogenized skin tissue was mixed with a sample solution (Bio-Rad, 161-0747) and inactivated at a temperature of 95° C. for 5 minutes. Thereafter, the protein was separated by a sodium dodecyl sulfate-polyacrylamide gel electrophoresis (SDS-PAGE) method, and then transferred to a nitrocellulose membrane. Treatment with anti-Sirt1 antibody (Abcam), anti-acetyl NF-κB p65 antibody and anti-acetyl p53 antibody (Cell Signaling Technologies), and anti-β-actin antibody (Santa Cruz Biotechnology) as primary antibodies were performed, and reaction was allowed to proceed. Then, secondary antibodies of Bethyl Laboratories, Inc. and a developing reagent (ECL solution, West Save Gold kit of AbFrontier, LF-QC0103) were used to identify expression level of the Sirt1 protein and acetylation reaction of the target proteins thereof, NF-κB p65 and p53.

As a result, a phenomenon was observed in which although in the skin tissue, cyclophosphamide has lead to decreased expression of Sirt1 protein and increased acetylation of the target proteins, NF-κB p65 and p53, combined treatment with dunnione normalizes Sirt1 expression and suppresses acetylation reaction of p65 and p53 (FIG. 9).

Example 4. Experimental Groups for Identifying Hair Loss Inhibitory Effect of Dunnione in Animal Model Having Alopecia Caused by Docetaxel, Adriamycin, and Cyclophosphamide In order to identify a hair loss inhibitory effect of dunnione in an animal model having combined chemotherapy-induced alopecia (CIA), animals were divided into four experimental groups and used for experiments. Docetaxel (DTX), adriamycin (ADR), and cyclophosphamide (CYP) were used as anticancer drugs, and combined administration of the three anticancer drugs was designated as TAC. In addition, information was obtained from the National Comprehensive Cancer Network (NCCN) for the single concentration (designated as 1× concentration) of each anticancer drug which is actually clinically applied to cancer patients. As described below, for the experimental group to be treated with anti-cancer drugs, the mice were treated with docetaxel, adriamycin, and cyclophosphamide at 6× concentration (11.58 mg/kg, 9.24 mg/kg, and 76.8 mg/kg, respectively). When treatment with the anticancer drugs is performed, the anticancer drugs were injected intraperitoneally at time intervals of 1 hour so that each of the anticancer drugs can be sufficiently absorbed.

Figure 10:
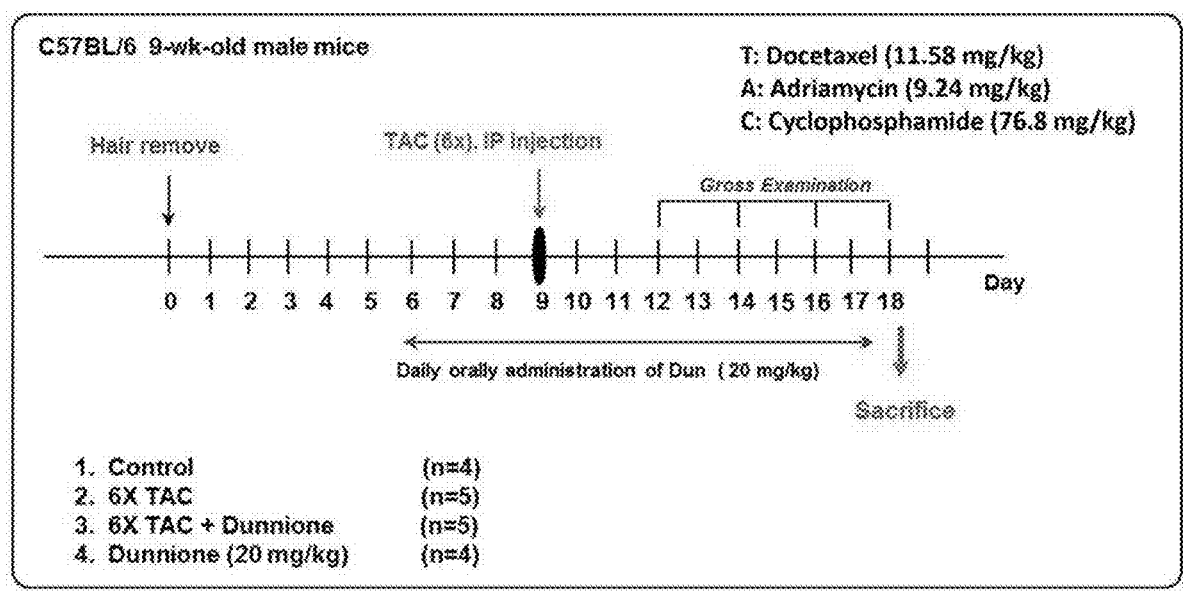
FIG. 10 illustrates an experimental plan for identifying a hair loss inhibitory effect of dunnione in an animal model having alopecia caused by docetaxel, adriamycin, and cyclophosphamide.

The day, on which the mice were hair-removed in Example 1, was set as day 0, and the animals were divided into the following groups: normal group (Control, 4 animals) in which only PBS is intraperitoneally injected on day 9; TAC group (6×TAC, 6 animals) in which 6×TAC is intraperitoneally injected on day 9; combination-treated group (6×TAC+Dunnione, 5 animals) in which dunnione is orally administered on a daily basis starting from 3 days prior to treatment with 6×TAC; and dunnione alone-treated group (Dunnione, 4 animals) in which only dunnione is administered (FIG. 10).

Experimental Example 7. Visual Observation of Skin in Animal Model Having Alopecia Caused by 6×TAC, Following Treatment with Dunnione The day, on which the mice were hair-removed in Example 1, was set as day 0; and hair growth-related visual characteristics, which are observed on the animal's skin in each of the experimental groups described in Example 4, were photographed using a digital camera on days 12, 14, 16, and 18.

Figure 11A:
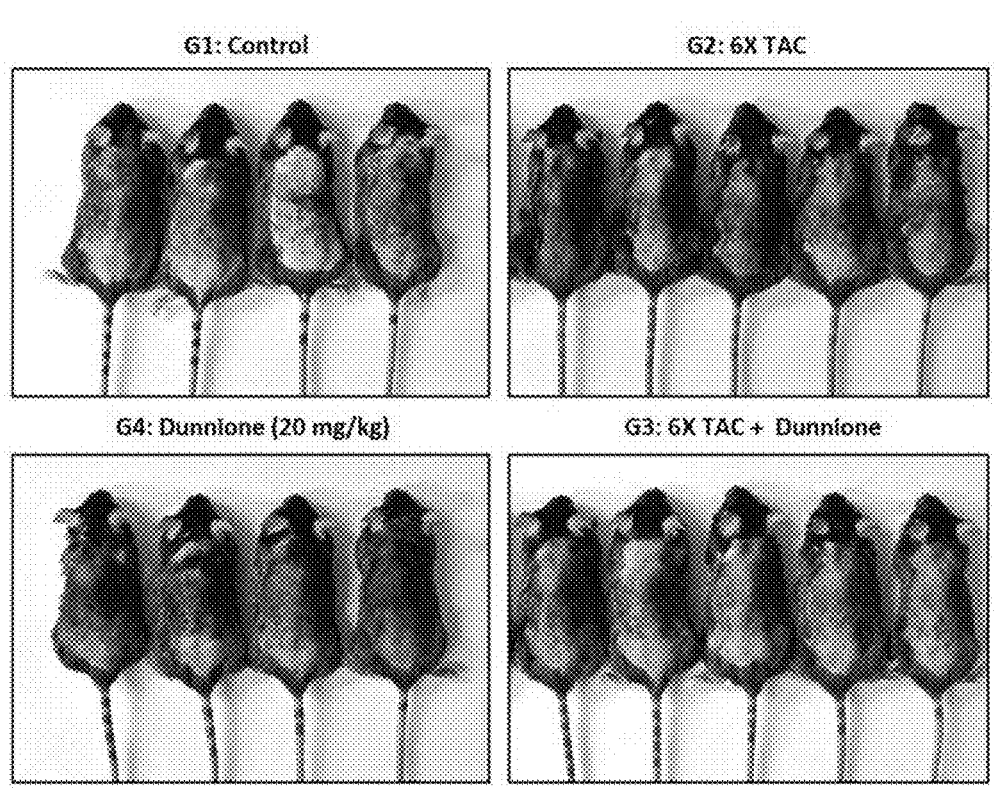
FIG. 11a illustrates results obtained by taking photographs of the skin surface for respective experimental groups on day 12 after hair removal in the animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).

In all experimental groups of Example 4, hair began to grow in a similar pattern on day 12 after hair removal (FIG. 11a).

Figure 11B:
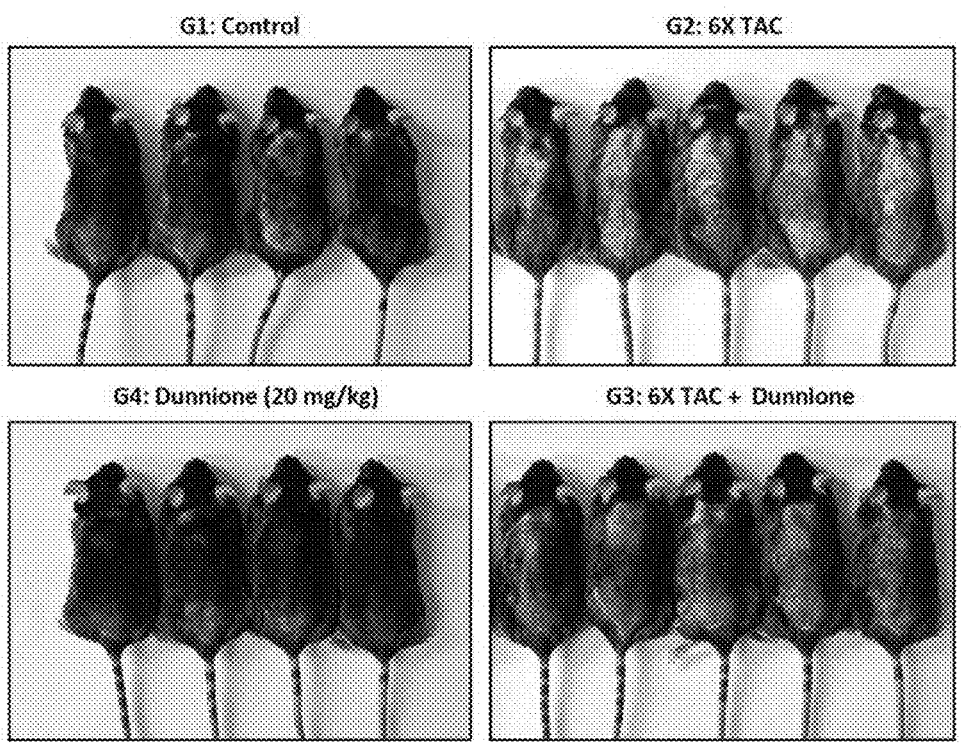
FIG. 11b illustrates results obtained by taking photographs of the skin surface for respective experimental groups on day 14 after hair removal in the animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).
Figure 12A:
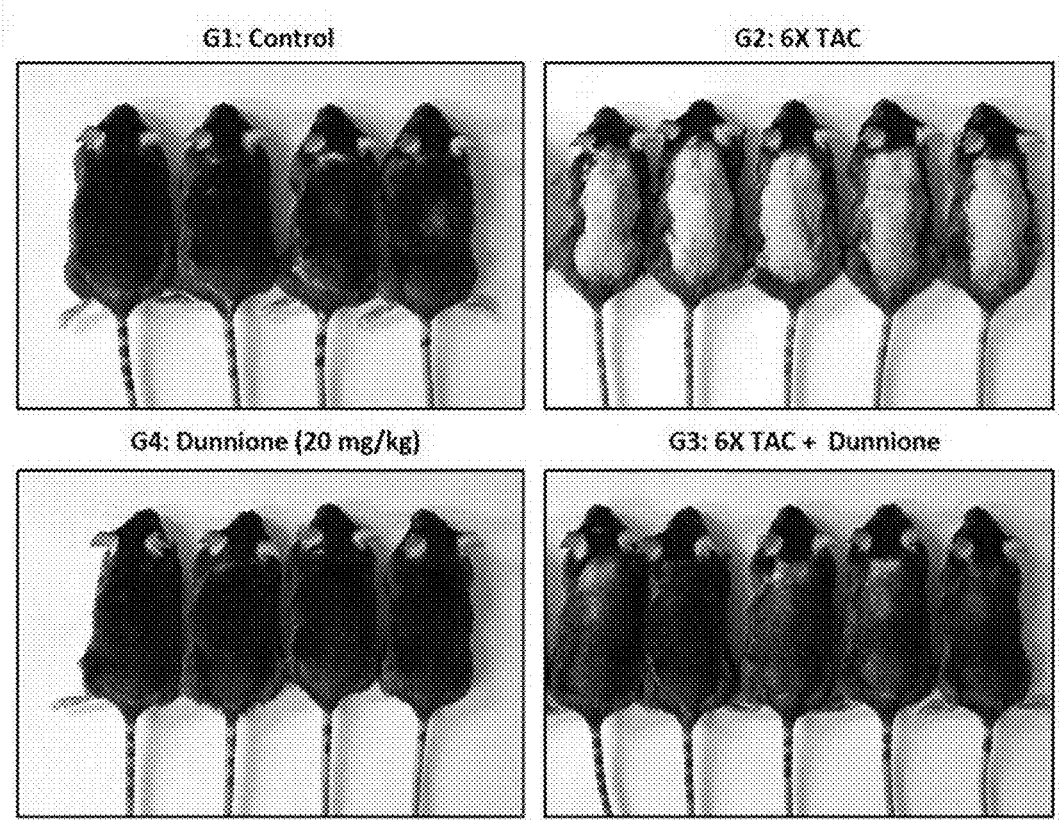
FIG. 12a illustrates results obtained by taking photographs of the skin surface for respective experimental groups on day 16 after hair removal in the animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).
Figure 12B:
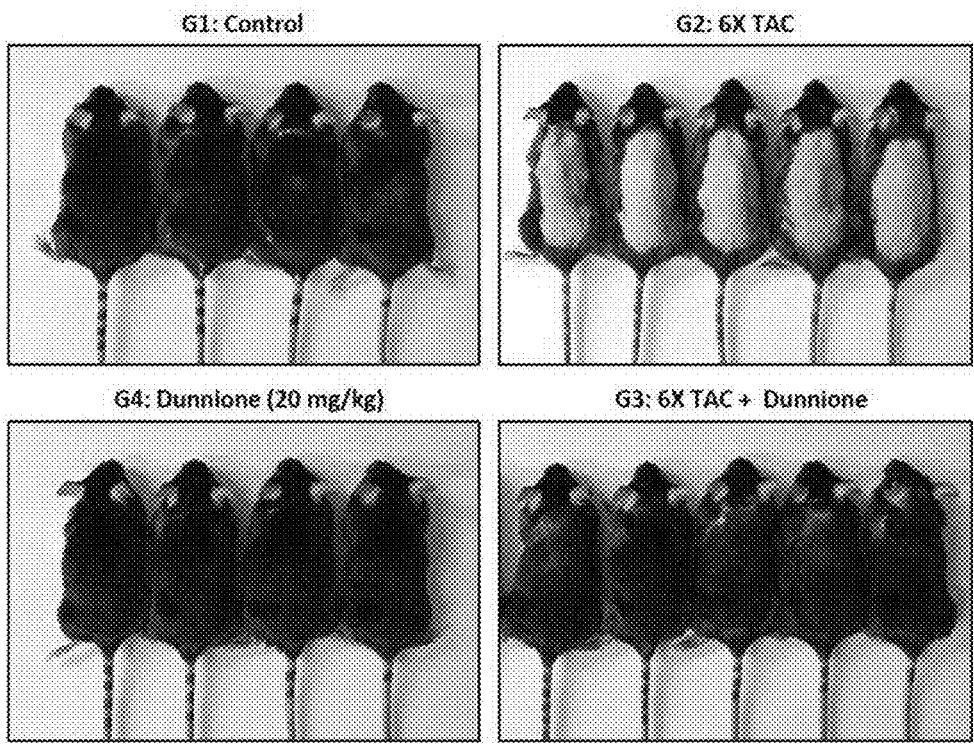
FIG. 12b illustrates results obtained by taking photographs of the skin surface for respective experimental groups on day 18 after hair removal in the animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).

On day 14 after hair removal, the dunnione plus 6×TAC combination-treated group (6×TAC+Dunnione) began to grow more hair than the 6×TAC alone-treated group (FIG. 11b). In addition, on day 18 after hair removal, in all experimental groups, except for the 6×TAC alone-treated group, hair grew overall so that the skin is full of hair and looks black (FIGS. 12a and 12b).

Experimental Example 8. Observation of Histological Changes in Skin in Animal Model Having Alopecia Caused by 6×TAC, Following Treatment with Dunnione The day, on which the mice were hair-removed in Example 1, was set as day 0, and the mice in each of the experimental groups described in Example 4 were sacrificed on day 18. Subsequently, the mouse dorsal skin was dissected parallel or perpendicular to the vertebral line, and removed. The removed skin was fixed with a Bouin's solution for 12 hours, subjected to dehydration, and embedded in paraffin. Then, the resulting product was prepared into 5-μm sections. The prepared sections were subjected to hematoxylin and eosin (H&E) staining, and histological changes in the skin in each experimental group were observed.

Figure 13:
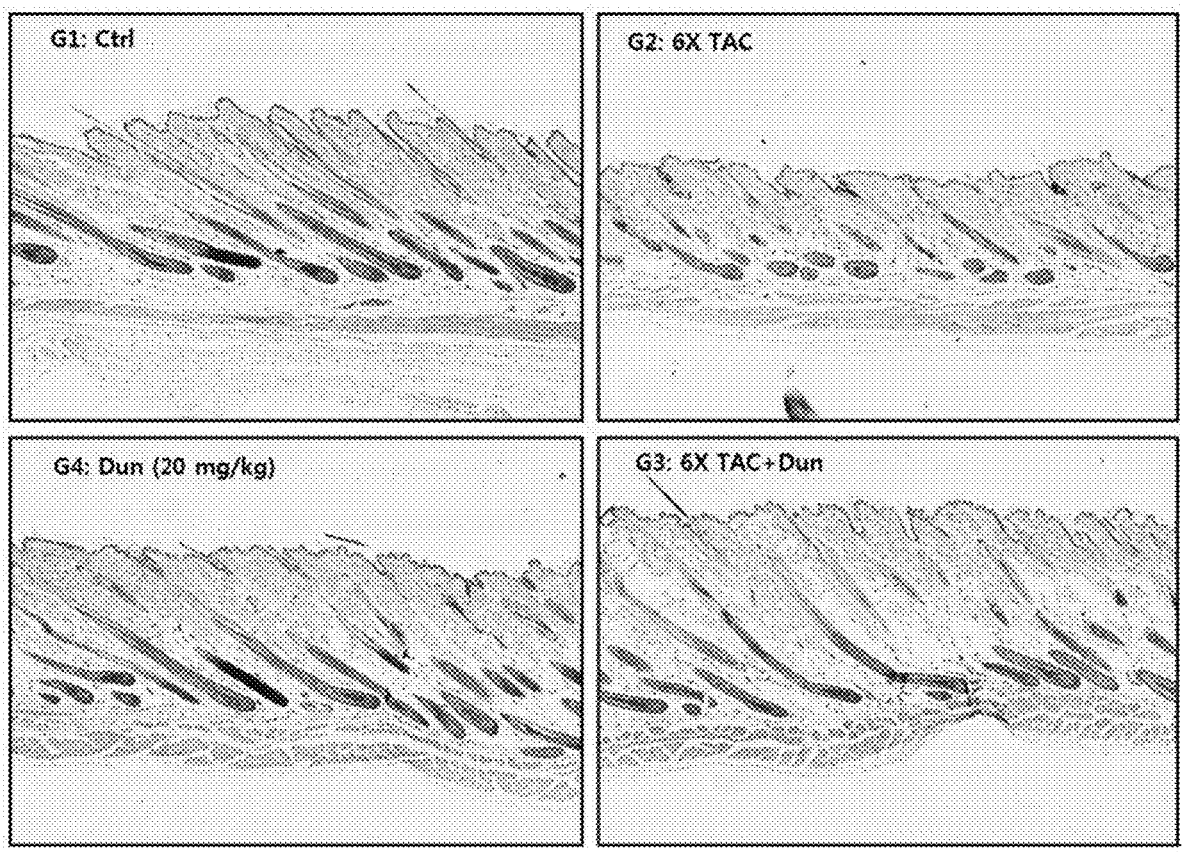
FIG. 13 illustrates results obtained by observing, with an optical microscope, the mouse skin surface on day 18 after hair removal in the animal model having alopecia caused by docetaxel, adriamycin, and cyclophosphamide: G1: Control (PBS-treated group); G2: 6×TAC (docetaxel (11.58 mg/kg), adriamycin (9.24 mg/kg), and cyclophosphamide (76.8 mg/kg)); G3: 6×TAC+Dunnione (6×TAC plus dunnione combination-treated group); G4: Dunnione (dunnione alone-treated group).

As a result, it was observed that in the 6×TAC alone-treated group (6×TAC), overall, the hair follicles have poorly developed or the inner root sheaths have insufficiently developed. On the other hand, it was observed that in the 6×TAC plus dunnione combination-treated group (6×TAC+Dunnione), the hair follicles and the inner root sheaths have well developed overall, and the number of growing hairs has increased as compared with the 6×TAC alone-treated group (FIG. 13).

Example 5. Experimental Groups for Identifying Relationship Between Hair Loss Inhibitory Effect of Dunnione and Enzyme NQO1 in Animal Model Having Alopecia Caused by Combined Treatment of Docetaxel, Adriamycin, and Cyclophosphamide In order to identify whether a hair loss inhibitory effect of dunnione in an animal model having combined chemotherapy-induced alopecia is dependent on the enzyme NQO1, the same experiments as described in Examples 1 and 2 were repeatedly performed using NQO1 knockout mice in place of the C57BL/6 mice.

The day, on which the NQO1 knockout mice were hair-removed according to Example 1, was set as day 0, and the animals were divided into the following experimental groups and used for experiments: normal group (Control, 3 animals) in which only PBS is intraperitoneally injected on day 9; administration group (6×TAC, 3 animals) in which docetaxel (11.58 mg/kg), adriamycin (9.24 mg/kg), and cyclophosphamide (76.8 mg/kg) are intraperitoneally injected on day 9; combination-treated group (6×TAC+Dunnione, 3 animals) in which dunnione is orally administered on a daily basis starting from 3 days prior to combined treatment of the anticancer drugs; and dunnione alone-treated group (Dunnione, 3 animals) in which only dunnione (20 mg/kg) is administered (FIG. 14).

Experimental Example 9. Visual Observation of Skin in NQO1 Knockout Mice, Following Treatment with Dunnione The day, on which the NQO1 knockout mice were hair-removed according to Example 1, was set as day 0; and hair growth-related visual characteristics, which are observed on the animal's skin in each of the experimental groups described in Example 5, were photographed using a digital camera on days 8, 12, 14, 16, and 18.

For the normal group (Control) injected with only PBS and the dunnione alone-treated group (Dunnione) in Example 5, hair began to grow starting from day 12 after hair removal and hair grew overall on day 18 so that the skin is full of hair and looks black, similar to the results seen with the C57BL/6 mice. On the other hand, for the docetaxel, adriamycin, and cyclophosphamide combination-treated group (6×TAC) and the 6×TAC plus dunnione combination-treated group (6×TAC+Dunnione), a phenomenon was observed in which hair hardly grows until day 18 after hair removal (FIG. 15).

Experimental Example 10. Observation of Histological Changes in Skin in NQO1 Knockout Mice, Following Treatment with Dunnione The day, on which the NQO1 knockout mice were hair-removed according to Example 1, was set as day 0, and the mice in each of the experimental groups described in Example 5 were sacrificed on day 18. Subsequently, the mouse dorsal skin was dissected parallel or perpendicular to the vertebral line, and removed. The removed skin was fixed with a Bouin's solution for 12 hours, subjected to dehydration, and embedded in paraffin. Then, the resulting product was prepared into 5-μm sections. The prepared sections were subjected to hematoxylin and eosin (H&E) staining, and histological changes in the skin in each experimental group were observed.

As a result, it was observed that in the normal group (Control) injected with only PBS and the dunnione alone-treated group (Dunnione), the hair follicles and inner root sheaths have well developed overall, similar to the results seen with the C57BL/6 mice, whereas it was observed that in the docetaxel, adriamycin, and cyclophosphamide-treated group (6×TAC) and the dunnione plus anticancer drugs combination-treated group (6×TAC+Dunnionee), overall, the hair follicles have poorly developed or the inner root sheaths have insufficiently developed (FIG. 16).

Based on the above results, it was identified that since dunnione causes, in an NQO1-dependent manner, rapid growth of hair follicles and shortened hair regrowth time, dunnione has an excellent effect on chemotherapy-induced alopecia.

The invention claimed is:

1. A method for preventing or ameliorating hair loss of a subject, comprising administering to the subject a composition comprising as an active ingredient a compound of Formula 1, a pharmaceutically acceptable salt thereof, a prodrug thereof, or a solvate thereof:

[Formula 1]

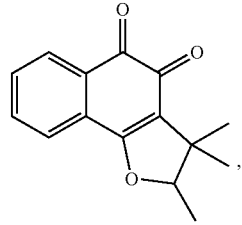

wherein the hair loss is caused by therapy with an anti-cancer drug.

2. The method of claim 1, wherein the anti-cancer drug is one or more selected from the group consisting of adriamycin, amsacrine, bleomycin, busulphan, cyclophosphamide, cytarabine, daunorubicin, docetaxel, epirubicin, etoposide, 5-fluorouracil, gemcitabine, ifosfamide, irinotecan, lomustine, melphalan, paclitaxel, thiotepa, topotecan, vinblastine, vindesine, and vinorelbine.

3. The method of claim 1, wherein the administering the composition suppresses loss of hair follicles and/or inner root sheaths.

4. The method of claim 1, wherein the administering the composition reduces hair loss and/or increases hair regrowth of the subject.

5. The method of claim 1, wherein the composition is a pharmaceutical composition.

6. The method of claim 1, wherein the subject had been treated with an anti-cancer drug or is under a treatment with an anti-cancer drug.

* * * * *